(12) United States Patent
Fan et al.

(10) Patent No.: US 11,254,695 B2
(45) Date of Patent: *Feb. 22, 2022

(54) SOLUBLE C5AR ANTAGONISTS

(71) Applicant: CHEMOCENTRYX, INC., Mountain View, CA (US)

(72) Inventors: Pingchen Fan, Fremont, CA (US); Antoni Krasinski, Sunnyvale, CA (US); Venkat Reddy Mali, Cupertino, CA (US); Shichang Miao, Foster City, CA (US); Sreenivas Punna, Sunnyvale, CA (US); Yang Song, Foster City, CA (US); Valentino J. Stella, Lawrence, KS (US); Yibin Zeng, Foster City, CA (US); Penglie Zhang, Foster City, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/660,994

(22) Filed: Oct. 23, 2019

(65) Prior Publication Data
US 2020/0262853 A1 Aug. 20, 2020

Related U.S. Application Data

(63) Continuation of application No. 16/357,889, filed on Mar. 19, 2019, now Pat. No. 10,487,098, which is a continuation of application No. 15/908,508, filed on Feb. 28, 2018, now Pat. No. 10,329,314, which is a continuation of application No. 15/477,386, filed on Apr. 3, 2017, now abandoned.

(60) Provisional application No. 62/317,721, filed on Apr. 4, 2016.

(51) Int. Cl.
| | |
|---|---|
| *C07F 9/6558* | (2006.01) |
| *C07F 9/59* | (2006.01) |
| *A61K 31/451* | (2006.01) |
| *A61K 31/496* | (2006.01) |
| *A61K 31/675* | (2006.01) |
| *A61K 45/06* | (2006.01) |
| *C07D 211/60* | (2006.01) |

(52) U.S. Cl.
CPC ........ *C07F 9/65583* (2013.01); *A61K 31/451* (2013.01); *A61K 31/496* (2013.01); *A61K 31/675* (2013.01); *A61K 45/06* (2013.01); *C07D 211/60* (2013.01); *C07F 9/59* (2013.01)

(58) Field of Classification Search
CPC ...... C07F 9/65583; C07F 9/59; C07D 211/06; A61K 31/451; A61K 31/496; A61K 31/675; A61K 45/06
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 5,985,856 | A | 11/1999 | Stella et al. |
| 7,572,795 | B2 | 8/2009 | Liu et al. |
| 8,106,209 | B2 | 1/2012 | Liu et al. |
| 8,901,106 | B2 | 12/2014 | Kick et al. |
| 9,586,953 | B2 | 3/2017 | Casillas et al. |
| 10,329,314 | B2 | 6/2019 | Fan et al. |
| 10,487,098 | B2 | 11/2019 | Fan et al. |
| 2008/0015157 | A1 | 1/2008 | Umeda et al. |
| 2009/0170956 | A1 | 7/2009 | Shen et al. |
| 2009/0304605 | A1 | 12/2009 | Liu et al. |

(Continued)

FOREIGN PATENT DOCUMENTS

| | | |
|---|---|---|
| EP | 2 065 358 A1 | 6/2009 |
| JP | 2001-527083 A | 12/2001 |

(Continued)

OTHER PUBLICATIONS

Extended European Search Report dated Oct. 24, 2019 corresponding to EP 17779588.7 filed Apr. 3, 2017; 8 pages.

(Continued)

*Primary Examiner* — Sahar Javanmard

(74) *Attorney, Agent, or Firm* — Mintz Levin Cohn Ferris Glovsky and Popeo PC

(57) ABSTRACT

Compounds are provided to modulate the C5a receptor. The compounds have the following Formula (I):

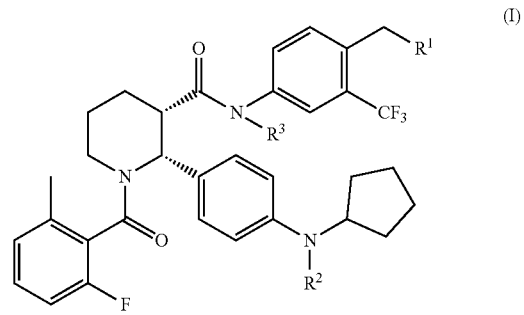

including stereoisomers and pharmaceutically acceptable salts thereof, wherein $R^1$, $R^2$ and $R^3$ are as defined herein. Methods associated with preparation and use of such compounds, as well as pharmaceutical compositions comprising such compounds, are also disclosed.

16 Claims, 1 Drawing Sheet

(56) References Cited

U.S. PATENT DOCUMENTS

| | | | |
|---|---|---|---|
| 2009/0304680 A1* | 12/2009 | Kuijpers | C12Q 1/6883 424/130.1 |
| 2010/0160320 A1 | 6/2010 | Fan et al. | |
| 2011/0275639 A1 | 11/2011 | Fan et al. | |
| 2013/0172347 A1 | 7/2013 | Fan et al. | |
| 2017/0283446 A1 | 10/2017 | Fan et al. | |

FOREIGN PATENT DOCUMENTS

| | | |
|---|---|---|
| JP | 2009-535295 A | 10/2009 |
| JP | 2010-502656 A | 1/2010 |
| JP | 2011-522838 A | 8/2011 |
| JP | 2014-510110 A | 4/2014 |
| JP | 2015-529681 A | 10/2015 |
| WO | 99/33846 A2 | 7/1999 |
| WO | 99/33846 A3 | 7/1999 |
| WO | 02/49993 A2 | 6/2002 |
| WO | 02/49993 A3 | 6/2002 |
| WO | 03/029187 A1 | 4/2003 |
| WO | 03/082826 A1 | 10/2003 |
| WO | 03/082828 A1 | 10/2003 |
| WO | 03/084524 A1 | 10/2003 |
| WO | 2004/018460 A1 | 3/2004 |
| WO | 2004/043925 A2 | 5/2004 |
| WO | 2004/043925 A3 | 5/2004 |
| WO | 2004/100975 A1 | 11/2004 |
| WO | 2005/007087 A2 | 1/2005 |
| WO | 2005/007087 A3 | 1/2005 |
| WO | 2007/103839 A2 | 9/2007 |
| WO | 2009/149436 A1 | 12/2009 |
| WO | 2010/075257 A1 | 7/2010 |
| WO | 2011/163640 A1 | 12/2011 |
| WO | 2012/135082 A1 | 10/2012 |
| WO | 2013/032964 A1 | 3/2013 |
| WO | 2014/043446 A1 | 3/2014 |
| WO | 2014/198647 A2 | 12/2014 |

OTHER PUBLICATIONS

Hageman, Gregory S. et al., "A common haplotype in the complement regulatory gene factor H (HF1/CFH) predisposes individuals to age-related macular degeneration," *PNAS* (May 17, 2005) 102(20):7227-7232.

Pan, Hao et al., "Anaphylatoxin C5a contributes to the pathogenesis of cisplatin-induced nephrotoxicity," *Am J Physiol Renal Physiol* (Jan. 14, 2009); 296:F496-F504.

Stella, Valentino J. et al., "Prodrug strategies to overcome poor water solubility," *Advanced Drug Delivery Reviews* (available online May 29, 2007); 59:677-694.

Strachan, Anna J. et al., "A New Small Molecule C5a Receptor Antagonist Inhibits the Reverse-Passive Arthus Reacton and Endotoxic Shock in Rats," *J Immunol* (2000; accepted for pub Apr. 6, 2000); 164:6560-6565.

Sumichika, Hiroshi et al., "Identification of a Potent and Orally Active Non-peptide C5a Receptor Antagonist," *The Journal of Biological Chemistry* (Dec. 20, 2002); 277(51):49403-49407.

Volanakis, John E., "Complement in vasculitis," Chapter 5, Vasculitis, Second Edition Ball and Bridges, Oxford University Press (© 2008); pp. 47-53.

Woodruff, Trent M. et al., "A Potent Human C5a Receptor Antagonist Protects against Disease Pathology in a Rat Model of Inflammatory Bowel Disease," *J Immunol* (2003; accepted for pub Sep. 9, 2003) 171:5514-5520.

Bundgaard, Hans et al., "Novel chemical approaches in prodrug design," *Drugs of the Future* © PROUS SCIENCE(1991) 16(5):443-458.

\* cited by examiner

SOLUBLE C5AR ANTAGONISTS

CROSS-REFERENCES TO RELATED APPLICATIONS

This application is a continuation of U.S. patent application Ser. No. 16/357,889 filed Mar. 19, 2019, which is a continuation of U.S. patent application Ser. No. 15/908,508 filed Feb. 28, 2018, which is a continuation of U.S. patent application Ser. No. 15/477,386 filed Apr. 3, 2017 (Abandoned), which is an application claiming benefit under 35 U.S.C. § 119(e) of U.S. Provisional Application No. 62/317,721 filed Apr. 4, 2016, each of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Non-peptide based C5a receptor antagonists have been described in the literature (e.g., Sumichika, H., et al., *J. Biol. Chem.* (2002), 277, 49403-49407), and have been reported as being effective for treating endotoxic shock in rats (Stracham, A. J., et al., *J. of Immunol.* (2000), 164(12): 6560-6565); and for treating IBD in a rat model (Woodruff, T. M., et al., *J of Immunol.*, 2003, 171: 5514-5520). Non-peptide based C5a receptor modulators also have been described in the patent literature by Neurogen Corporation, (e.g., WO 2004/043925, WO 2004/018460, WO 2005/007087, WO 03/082826, WO 03/08828, WO 02/49993, WO 03/084524); Dompe S.P.A. (WO 02/029187); The University of Queenland (WO 2004/100975); and ChemoCentryx, Inc. (WO 2010/075257 and WO 2011/163640).

There is considerable experimental evidence in the literature that implicates increased levels of C5a with a number of diseases and disorders, in particular in autoimmune and inflammatory diseases and disorders. There is a need in the art for new small organic molecule modulators, e.g., agonists, partial agonists, and preferably antagonists, of the C5a receptor (C5aR) that are useful for inhibiting pathogenic events, e.g., chemotaxis, associated with increased levels anaphylatoxin activity.

Despite the availability of C5aR antagonist compounds as described in WO 2010/075257 and WO 2011/163640, there remains a need for related compounds having improved solubility profiles that can be formulated in a manner suitable for intravenous delivery and also provide a therapeutic benefit similar to the compounds in WO 2010/075257 and WO 2011/163640.

BRIEF SUMMARY OF THE INVENTION

In one aspect, provided herein are compounds having formula (I):

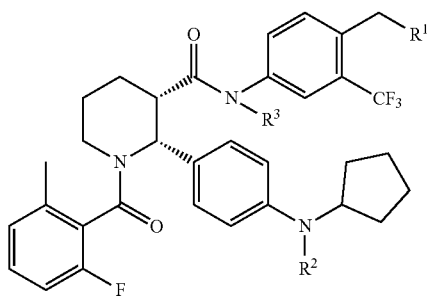

or a pharmaceutically acceptable salt thereof, wherein:
$R^1$ is selected from the group consisting of H, —O—$CH_2$—O—P(O)$OR^aOR^b$, —O—C(O)—$C_{1-6}$ alkylene-$L^2$-$X^1$, O—P(O)$OR^aOR^b$, and —O—C(O)-$A^1$-($C_{1-3}$ alkylene)$_n$-$C_{4-7}$ heterocyclyl wherein the $C_{4-7}$ heterocyclyl is optionally substituted with 1 to 6 $R^c$ groups;
$A^1$ is selected from the group consisting of $C_{6-10}$ aryl, $C_{3-10}$ cycloalkyl, $C_{5-10}$ heteroaryl and $C_{5-10}$ heterocyclyl, each of which is optionally substituted with 1 to 5 $R^x$ which can be the same or different;
n is 0 or 1;
$L^2$ is selected from the group consisting of a bond, —O—C(O)—$C_{1-6}$ alkylene-, and —$NR^d$—C(O)—$C_{1-6}$ alkylene-;
$X^1$ is independently selected from the group consisting of —$NR^eR^f$, —P(O)$OR^aOR^b$, —O—P(O)$OR^aOR^b$, and —$CO_2H$;
$R^2$ is selected from the group consisting of H, -$L^3$-$C_{1-6}$ alkylene-$L^4$-$X^2$, -$L^3$-($C_{1-6}$ alkylene)$_m$-$A^2$-$X^2$, —P(O)$OR^aOC(O)$—$C_{1-6}$ alkyl, —P(O)$OR^aNR^gR^h$ and —P(O)$OR^aOR^b$;
$L^3$ is independently selected from the group consisting of —C(O)—O—, and —C(O)—;
$L^4$ is independently selected from the group consisting of a bond, —O—C(O)—$C_{2-6}$ alkenylene-, —O—C(O)—$C_{1-6}$ alkylene-, and —$NR^d$—C(O)—$C_{1-6}$ alkylene- wherein the $C_{1-6}$ alkylene in —$NR^d$—C(O)—$C_{1-6}$ alkylene- and —O—C(O)—$C_{1-6}$ alkylene- is optionally substituted with $NR^eR^f$;
$X^2$ is independently selected from the group consisting of —$NR^kR^l$, —P(O)$OR^aOR^b$, —O—P(O)$OR^aOR^b$, and —$CO_2H$;
m is 0 or 1;
$A^2$ is selected from the group consisting of $C_{6-10}$ aryl, $C_{3-10}$ cycloalkyl, $C_{5-10}$ heteroaryl and $C_{5-10}$ heterocyclyl, each of which is optionally substituted with 1 to 5 $R^x$ which can be the same or different;
$R^3$ is H or -$L^5$-P(O)$OR^aOR^b$ wherein $L^5$ is independently selected from the group consisting of a bond and —$CH_2$—O—;
each $R^x$ is independently selected from the group consisting of halogen, $C_{1-6}$alkyl, $C_{1-6}$haloalkyl, $C_{1-6}$heteroalkyl, CN, $NR^yR^z$, $SR^y$ and $OR^y$;
each $R^c$ is independently selected from the group consisting of halogen, $C_{1-6}$alkyl, $C_{1-6}$haloalkyl, $C_{1-6}$heteroalkyl, CN, $NR^yR^z$, $SR^y$ and $OR^y$;
each $R^a$, $R^b$, $R^d$, $R^e$, $R^f$, $R^g$, $R^k$, $R^l$, $R^y$ and $R^z$ is independently selected from the group consisting of H and $C_{1-6}$ alkyl;
each $R^h$ is independently selected from the group consisting of H and $C_{1-6}$ alkyl wherein the $C_{1-6}$ alkyl is optionally substituted with 1 to 5 substituents independently selected from $CO_2H$, $NR^iR^j$, $C_{6-10}$ aryl, $C_{3-10}$ cycloalkyl, $C_{5-10}$ heteroaryl and $C_{5-10}$ heterocyclyl, wherein each $R^i$ and $R^j$ is independently H or $C_{1-6}$ alkyl; and wherein two of $R^1$, $R^2$ and $R^3$ are H, and one of $R^1$, $R^2$ and $R^3$ is other than H.

In addition to the compounds provided herein, the present invention further provides pharmaceutical compositions containing one or more of these compounds, as well as methods for the use of these compounds in therapeutic methods, primarily to treat diseases associated with C5a signaling activity.

DETAILED DESCRIPTION OF THE INVENTION

I. Abbreviation and Definitions

Figure 1:
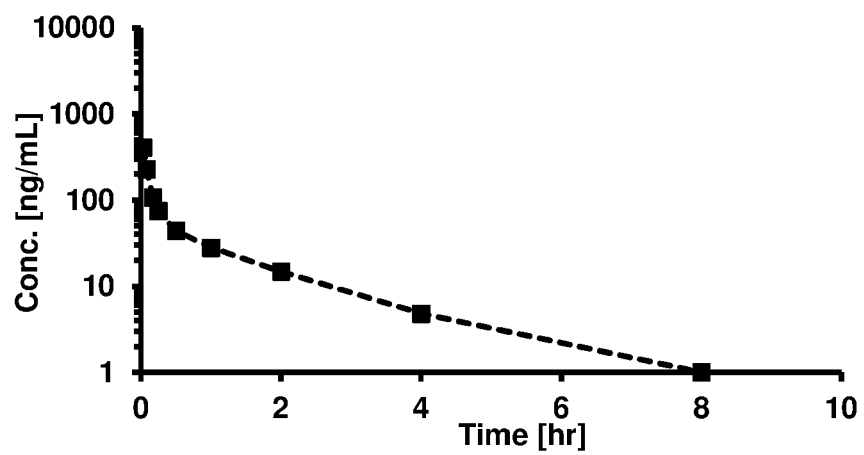
FIG. 1 is a graph showing the release of an active compound 1.543 (from WO 2011/163640) from the compound of Example 22.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkyl" in its broadest sense is also meant to include those unsaturated groups such as alkenyl and alkynyl groups. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" or "heterocyclyl" refers to a cycloalkyl group that contain from one to five heteroatoms as ring vertices selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substituents on the carbon that is closest to the point of attachment for the radical is replaced with the substituent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts. Certain specific compounds of the present disclosure contain more than one acidic functionality or more than one basic functionality. In those cases, the term "or a pharmaceutically acceptable salt thereof" is meant to encompass multi-salt compounds, for example a di Na salt, a di HCl salt.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present invention.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown (e.g., dashed or wedge bonds), it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present invention. For example, the compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present invention.

II. Compounds

In one aspect, the present invention provides compounds having formula (I):

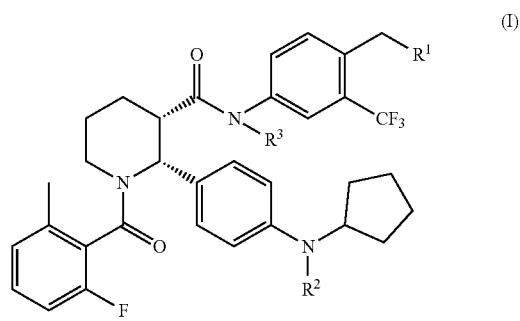

(I)

or a pharmaceutically acceptable salt thereof, wherein:

$R^1$ is selected from the group consisting of H, —O—CH$_2$—O—P(O)OR$^a$OR$^b$, —O—C(O)—C$_{1-6}$ alkylene-L$^2$-X$^1$, O—P(O)OR$^a$OR$^b$, and —O—C(O)-A$^1$-(C$_{1-3}$ alkylene)$_n$-C$_{4-7}$ heterocyclyl wherein the C$_{4-7}$ heterocyclyl is optionally substituted with 1 to 6 R$^c$ groups;

A$^1$ is selected from the group consisting of C$_{6-10}$ aryl, C$_{3-10}$ cycloalkyl, C$_{5-10}$ heteroaryl and C$_{5-10}$ heterocyclyl, each of which is optionally substituted with 1 to 5 R$^x$ which can be the same or different;

n is 0 or 1;

L$^2$ is selected from the group consisting of a bond, —O—C(O)—C$_{1-6}$ alkylene-, and —NR$^d$—C(O)—C$_{1-6}$ alkylene-;

$X^1$ is independently selected from the group consisting of —$NR^eR^f$, —$P(O)OR^aOR^b$, —O—$P(O)OR^aOR^b$, and —$CO_2H$;

$R^2$ is selected from the group consisting of H, -$L^3$-$C_{1-6}$ alkylene-$L^4$-$X^2$, -$L^3$-$(C_{1-6}$ alkylene$)_m$-$A^2$-$X^2$, —$P(O)OR^aOC(O)$—$C_{1-6}$ alkyl, —$P(O)OR^aNR^gR^h$ and —$P(O)OR^aOR^b$;

$L^3$ is independently selected from the group consisting of —C(O)—O—, and —C(O)—;

$L^4$ is independently selected from the group consisting of a bond, —O—C(O)—$C_{2-6}$ alkenylene-, —O—C(O)—$C_{1-6}$ alkylene-, and —$NR^d$—C(O)—$C_{1-6}$ alkylene- wherein the $C_{1-6}$ alkylene in —$NR^d$—C(O)—$C_{1-6}$ alkylene- and —O—C(O)—$C_{1-6}$ alkylene- may be optionally substituted with $NR^eR^f$;

$X^2$ is independently selected from the group consisting of —$NR^kR^l$, —$P(O)OR^aOR^b$, —O—$P(O)OR^aOR^b$, and —$CO_2H$;

m is 0 or 1;

$A^2$ is selected from the group consisting of $C_{6-10}$ aryl, $C_{3-10}$ cycloalkyl, $C_{5-10}$ heteroaryl and $C_{5-10}$ heterocyclyl, each of which is optionally substituted with 1 to 5 $R^x$ which can be the same or different;

$R^3$ is H or -$L^5$-$P(O)OR^aOR^b$ wherein $L^5$ is independently selected from the group consisting of a bond and —$CH_2$—O—;

each $R^x$ is independently selected from the group consisting of halogen, $C_{1-6}$alkyl, $C_{1-6}$haloalkyl, $C_{1-6}$heteroalkyl, CN, $NR^yR^z$, $SR^y$ and $OR^y$;

each $R^c$ is independently selected from the group consisting of halogen, $C_{1-6}$alkyl, $C_{1-6}$haloalkyl, $C_{1-6}$heteroalkyl, CN, $NR^yR^z$, $SR^y$ and $OR^y$;

each $R^a$, $R^b$, $R^d$, $R^e$, $R^f$, $R^g$, $R^k$, $R^l$, $R^y$ and $R^z$ is independently selected from the group consisting of H and $C_{1-6}$ alkyl;

each $R^h$ is independently selected from the group consisting of H and $C_{1-6}$ alkyl wherein the $C_{1-6}$alkyl is optionally substituted with 1 to 5 substituents independently selected from $CO_2H$, $NR^iR^j$, $C_{6-10}$ aryl, $C_{3-10}$ cycloalkyl, $C_{5-10}$ heteroaryl and $C_{5-10}$ heterocyclyl, wherein each $R^i$ and $R^j$ is independently H or $C_{1-6}$ alkyl; and wherein two of $R^1$, $R^2$ and $R^3$ are H, and one of $R^1$, $R^2$ and $R^3$ is other than H.

In one group of embodiments, compounds are provided of formula (I) or a pharmaceutically acceptable salt thereof, wherein $R^1$ is selected from the group consisting of O—(CO)—$C_{1-6}$ alkylene-$NR^eR^f$, O—(CO)—$C_{1-6}$ alkylene-$NR^d(CO)$—$C_{1-6}$ alkylene-$NR^eR^f$, O—$P(O)OR^aOR^b$, O—$CH_2$—O—$P(O)OR^aOR^b$ and O—(CO)—$C_{6-10}$arylene-$C_{1-3}$ alkylene-$C_{4-7}$ heterocyclyl, wherein the $C_{4-7}$ heterocyclyl is selected from the group consisting of piperidinyl, piperazinyl, pyrrolidinyl, morpholinyl and azetidinyl and wherein the piperidinyl, piperazinyl, pyrrolidinyl, morpholinyl and azetidinyl are optionally substituted with 1 to 6 $R^c$ groups.

In another group of embodiments, compounds are provided of formula (I) or a pharmaceutically acceptable salt thereof, wherein $R^1$ is selected from the group consisting of:

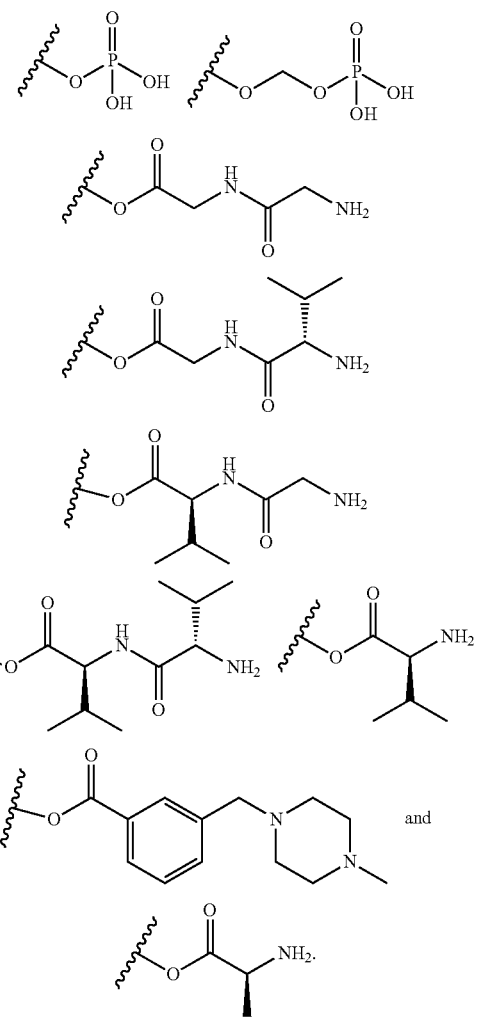

In yet another group of embodiments, compounds are provided of formula (I) or a pharmaceutically acceptable salt thereof, wherein $R^1$ is selected from the group consisting of:

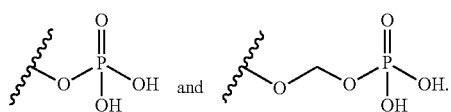 [SMILES: *OP(=O)(O)O ; *OCOP(=O)(O)O]

In still another group of embodiments, compounds are provided of formula (I) or a pharmaceutically acceptable salt thereof, wherein $R^1$ is

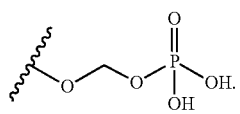 [SMILES: *OCOP(=O)(O)O]

In another group of embodiments, compounds are provided of formula (I) or a pharmaceutically acceptable salt thereof, wherein $R^1$ is

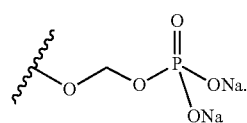

In still other embodiments, compounds are provided of formula (I) or a pharmaceutically acceptable salt thereof, wherein $R^3$ is selected from the group consisting of —$CH_2$—O—P(O)$OR^aOR^b$ and —P(O)$OR^aOR^b$.

In yet another group of embodiments, compounds are provided of formula (I) or a pharmaceutically acceptable salt thereof, wherein $R^3$ is selected from the group consisting of:

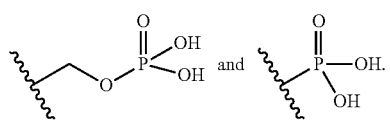 [SMILES: *COP(=O)(O)O ; *P(=O)(O)O]

In still another group of embodiments, compounds are provided of formula (I) or a pharmaceutically acceptable salt thereof, wherein $R^3$ is

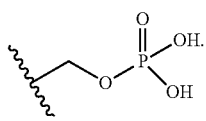 [SMILES: *COP(=O)(O)O]

In another group of embodiments, compounds are provided of formula (I) or a pharmaceutically acceptable salt thereof, wherein $R^3$ is

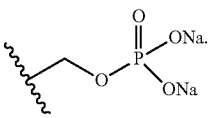

In other embodiments, compounds are provided of formula (I) or a pharmaceutically acceptable salt thereof, wherein $R^2$ is selected from the group consisting of —(CO)—$C_{1-6}$ alkylene-$NR^kR^l$, —(CO)—O—$C_{1-6}$ alkylene-O—P(O)$OR^aOR^b$, —P(O)$OR^aO$(CO)—$C_{1-6}$ alkyl, —P(O)$OR^aNR^gR^h$, (CO)—O—$C_{1-6}$ alkylene-O—(CO)—$C_{2-6}$ alkenylene-$CO_2H$, —(CO)—$C_{1-6}$ alkylene-$NR^d$(CO)—$C_{1-6}$ alkylene-$NR^kR^l$ wherein the $C_{1-6}$ alkylene-$NR^kR^l$ may be optionally substituted by with $NR^eR^f$, —(CO)—O—$C_{1-6}$ alkylene-O—(CO)— $C_{1-6}$ alkylene-$NR^kR^l$, and —(CO)—O—$C_{1-6}$ alkylene-$C_{6-10}$ aryl-O—P(O)$OR^aOR^b$ wherein the $C_{6-10}$ aryl is optionally substituted with 1 to 5 $R^x$ which can be the same or different.

In certain selected embodiments, $R^2$ is selected from the group consisting of:

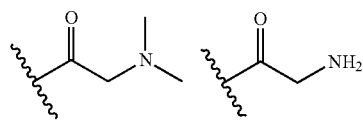

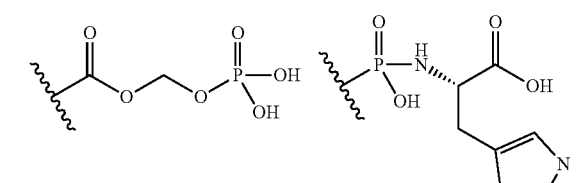

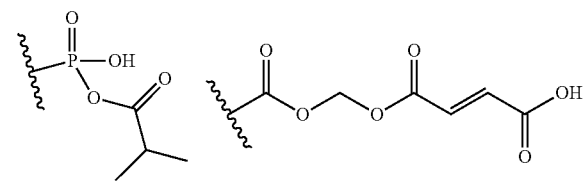

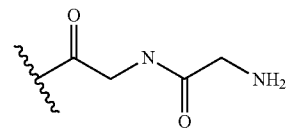

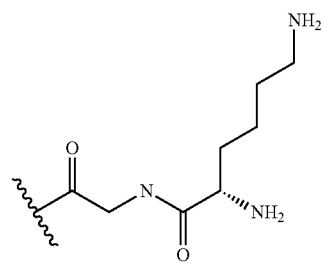

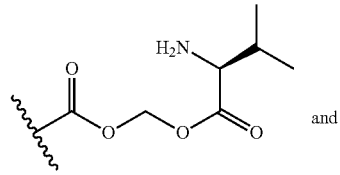

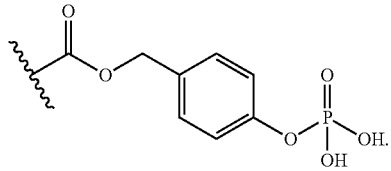

In selected embodiments, compounds are provided selected from the group consisting of:

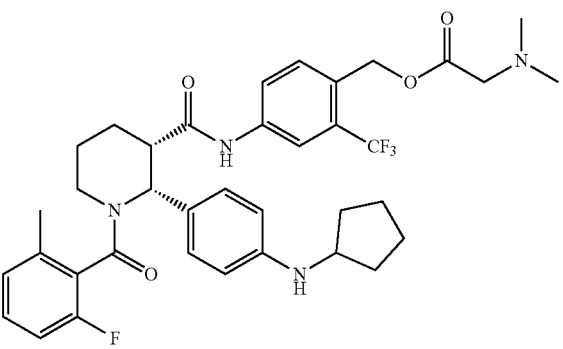

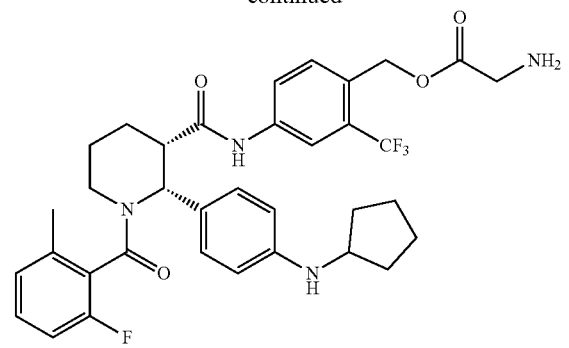
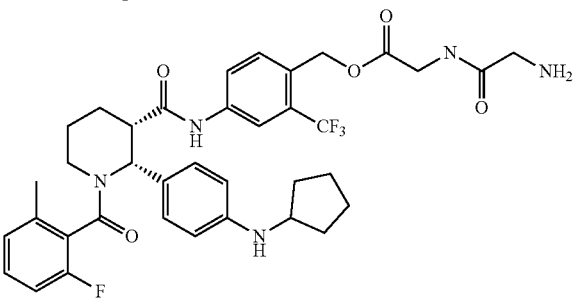
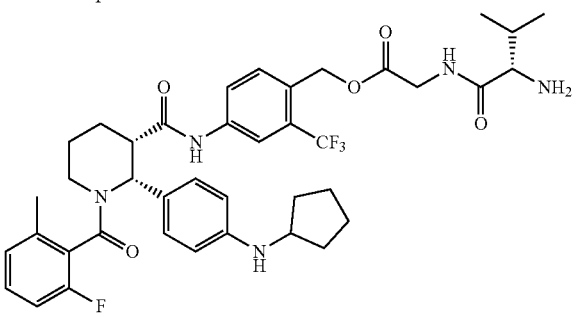
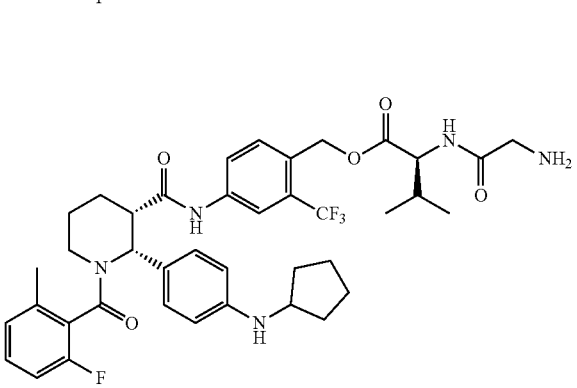
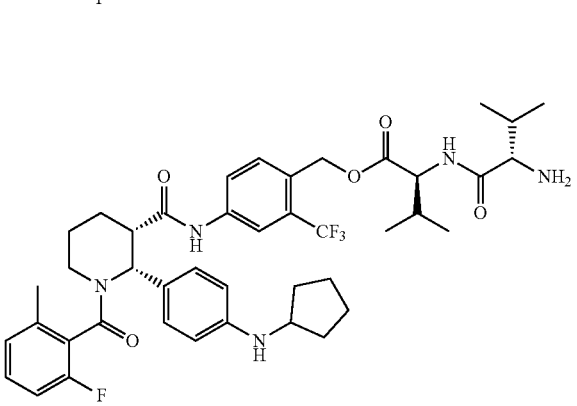
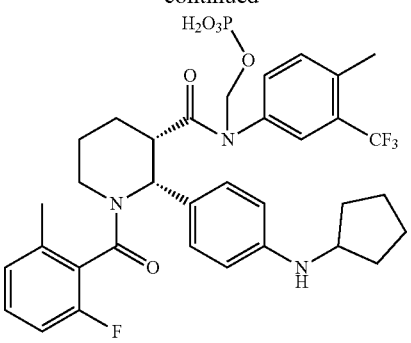
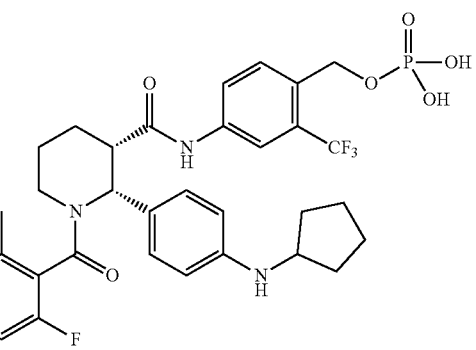
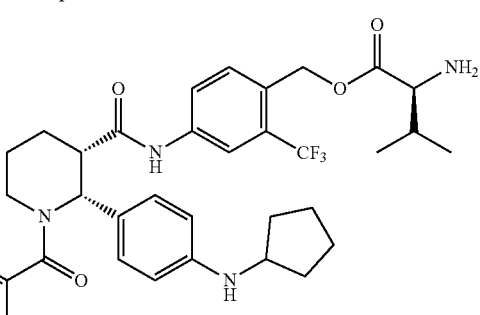
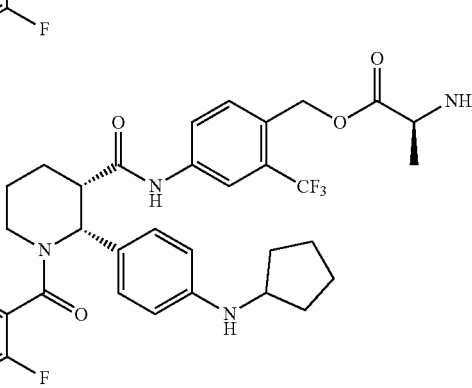
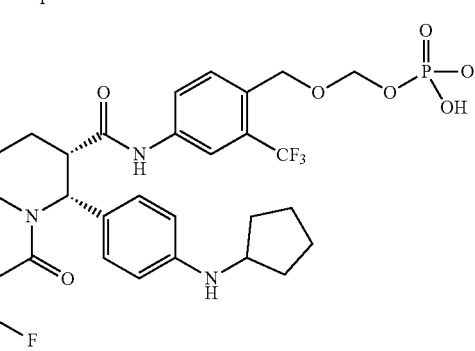

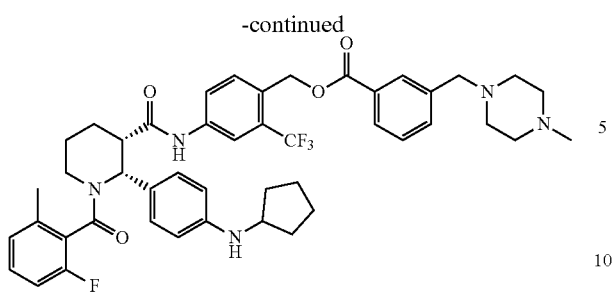
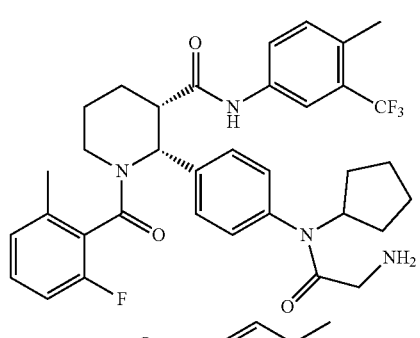
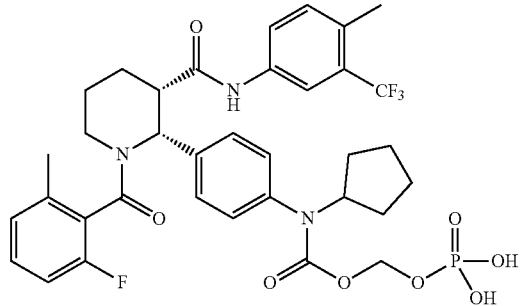
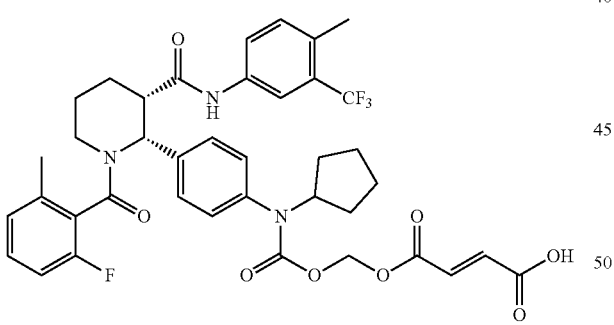
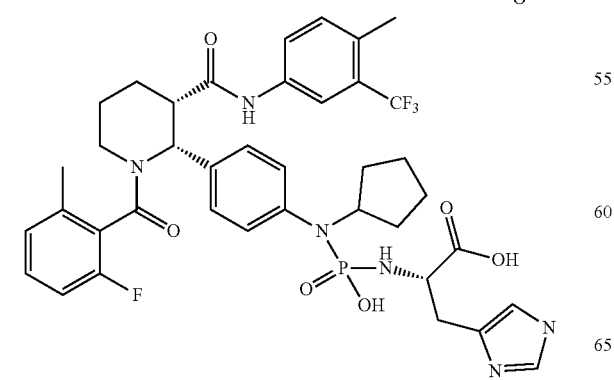
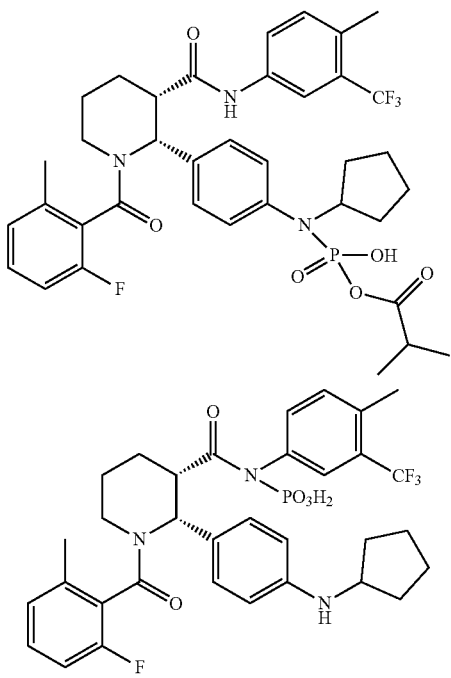
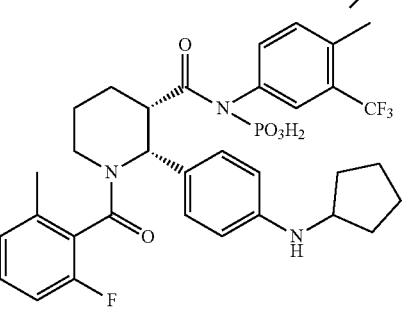
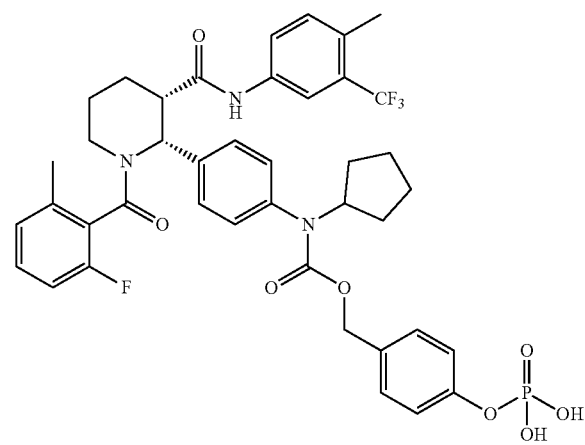
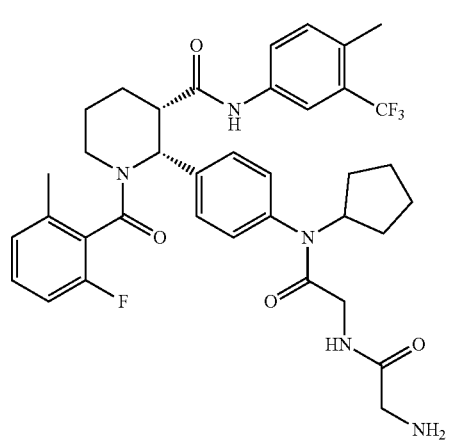

or a pharmaceutically acceptable salt thereof.

In addition to the compounds provided above, pharmaceutically acceptable salts of those compounds are also provided. In some embodiments, the pharmaceutically acceptable salts are selected from ammonium, calcium, magnesium, potassium, sodium, zinc, arginine, betaine, caffeine, choline, N,N'-dibenzylethyl enediamine, diethylamine, 2-diethyl aminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, procaine, purines, theobromine, triethylamine, trimethylamine, tripropylamine, tromethamine, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are selected from ammonium, calcium, magnesium, potassium, sodium, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are sodium or hydrochloric.

III. Pharmaceutical Compositions

In addition to the compounds provided above, compositions for modulating C5aR activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions contain the active materials in admixture with excipients suitable for the manufacture of aqueous suspensions. Such excipients are suspending agents, for example sodium carboxymethyl cellulose, methylcellulose, hydroxy-propylmethyl cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compounds of this disclosure may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

A pharmaceutical composition comprising a compound of the disclosure or a pharmaceutically acceptable salt thereof, and a pharmaceutically acceptable excipient is provided.

In some embodiments, the pharmaceutical composition is formulated for intravenous administration.

In some embodiments, the pharmaceutical composition comprises one or more additional therapeutic agents.

In some embodiments, the one or more additional therapeutic agent is selected from the group consisting of corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C is subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, CCR5 chemokine antagonists, CCR2 chemokine antagonists, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, CXCR1 chemokine antagonists, CXCR4 chemokine antagonists, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, and T cell receptor antagonists, and combinations thereof.

In some embodiments, the one or more additional therapeutic agent is selected from the group consisting of inhibitors of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

In some embodiments, the one or more additional therapeutic agent is selected from the group consisting of modulators of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX3CR1, and ChemR23.

In some embodiments, the one or more additional therapeutic agent is selected from the group consisting of corticosteroids, steroids, CD20 inhibitors and immunosuppressants. In some embodiments, the one or more additional therapeutic agent is an immunosuppressant. In some embodiments, the one or more additional therapeutic agent is a corticosteroid or steroid. In some embodiments, the one or more additional therapeutic agent is a CD20 inhibitor. In some embodiments, the one or more additional therapeutic agent is a corticosteroid or steroid and an immunosuppressant or a CD20 inhibitor. In some embodiments, the one or more additional therapeutic agent is a corticosteroid or steroid and an immunosuppressant. In some embodiments, the one or more additional therapeutic agent is a corticosteroid or steroid and a CD20 inhibitor.

In some embodiments, the one or more additional therapeutic agent is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+ propagermanium, ApoCell, cannabidiol, RGI-2001, saratin, anti-CD3 bivalent antibody-diphtheria toxin conjugate, NOX-100, and LT-1951.

In some embodiments, the one or more additional therapeutic agent is selected from the group consisting of OMS721, ALN-CC5, ACH-4471, AMY-101, Acthar gel, CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, KY-1003, CA-327 and CD4+CD25+ regulatory T-cells, and combinations thereof.

In some embodiments, the one or more additional therapeutic agent is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate.

In some embodiments, the one or more additional therapeutic agent is rituximab or cyclophosphamide. In some embodiments, the one or more additional therapeutic agent is rituximab. In some embodiments, the one or more additional therapeutic agent is cyclophosphamide. In some embodiments, the one or more additional therapeutic agent is prednisone. In some embodiments, the one or more additional therapeutic agent is rituximab or cyclophosphamide and prednisone.

IV. Methods of Treating Diseases and Disorders Modulated by C5a

The compounds of the disclosure may be used to generate active metabolites in vivo that are agonists, (preferably) antagonists, partial agonists, inverse agonists, of C5a receptors. In one embodiment, the compounds of the disclosure can be used to generate active metabolites, that are C5aR antagonists, to inhibit the binding of C5a receptor ligand (e.g., C5a) to C5a receptor in vivo.

Preferably, the amount of C5a receptor modulator generated from the compounds of this disclosure contacted with the receptor should be sufficient to inhibit C5a binding to C5a receptor.

In another embodiment, the compounds of the present disclosure further can be used for treating patients suffering from conditions that are responsive to C5a receptor modulation. As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). As used herein, a condition is considered "responsive to C5a receptor modulation" if modulation of C5a receptor activity results in the reduction of inappropriate activity of a C5a receptor. As used herein, the term "patients" include primates (especially humans), domesticated companion animals (such as dogs, cats, horses, and the like) and livestock (such as cattle, pigs, sheep, and the like), with dosages as described herein.

Conditions that can be Treated by C5a Modulation:

Autoimmune disorders—e.g., Rheumatoid arthritis, systemic lupus erythematosus, Guillain-Barre syndrome, pancreatitis, lupus nephritis, lupus glomerulonephritis, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, aHUS (Atypical Hemolytic Uremic Syndrome), Goodpasture's syndrome (and associated glomerulonephritis and pulmonary hemorrhage), immunovasculitis, tissue graft rejection, hyperacute rejection of transplanted organs; and the like.

Inflammatory disorders and related conditions—e.g., Neutropenia, sepsis, septic shock, Alzheimer's disease, multiple sclerosis, stroke, inflammatory bowel disease (IBD), age-related macular degeneration (AMD, both wet and dry forms), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, IGA nephropathy, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. Compounds of the instant disclosure may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a compound of the disclosure may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—Vasculitic dseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The compounds provided in the present disclosure can be used to treat ANCA vasculitis (anti-neutrophil cytoplasmic autoantibody vasculitis). The compounds provided in the present disclosure can be used to treat leukoclastic vasculitis, urticarial vasculitis, Wegener's granulomatosis, microscopic polyangiitis, Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—C5a receptor modulators provided herein may be used to inhibit HIV infection, delay AIDS progression or decrease the severity of symptoms or HIV infection and AIDS.

Neurodegenerative disorders and related diseases—Within further aspects, C5a antagonists provided herein may be used to treat Alzheimer's disease, multiple sclerosis, and cognitive function decline associated with cardiopulmonary bypass surgery and related procedures.

Cancers—The C5a antagonists provided herein are also useful for the treatment of cancers and precancerous conditions in a subject. Specific cancers that can be treated include, but are not limited to of melanomas, lung cancer, lymphomas, sarcomas, carcinomas, and mixed tumors. Exemplary conditions that may be treated according to the present disclosure include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas. In some embodiments, the disease or disorder is selected from the group consisting of glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, and carcinoma.

In another embodiment, the compounds of the present disclosure are useful in the treatment of cisplatin induced nephrotoxicity. In this embodiment, compound treatment can alleviate the nephrotoxicity induced by cisplatin chemotherapy of malignancies (Hao Pan et al, *Am J Physiol Renal Physiol,* 296, F496-504, 2009).

In one embodiment of the invention, the compounds of the disclosure can be used for the treatment of diseases selected from the group consisting of sepsis (and associated disorders), COPD, rheumatoid arthritis, lupus nephritis and multiple sclerosis.

Provided herein is a method of treating a human suffering from or susceptible to a disease or disorder involving pathologic activation of C5a receptors, comprising administering to the mammal a therapeutically effective amount of a compound of the disclosure or a pharmaceutical composition thereof.

Provided herein is a method of inhibiting C5a receptor-mediated cellular chemotaxis comprising contacting mammalian white blood cells with a C5a receptor modulatory amount of an active metabolite of a compound of the disclosure.

In some embodiments, the disease or disorder is an inflammatory disease or disorder, a cardiovascular or cerebrovascular disorder, an autoimmune disease, or an oncologic disease or disorder.

In some embodiments, the disease or disorder is selected from the group consisting of neutropenia, neutrophilia, C3-glomerulopathy, C3-glomerulonephritis, dense deposit disease, membranoproliferative glomerulonephritis, Kawasaki disease, sepsis, septic shock, Hemolytic uremic syndrome, atypical hemolytic uremic syndrome (aHUS), Alzheimer's disease, multiple sclerosis, stroke, inflammatory bowel disease, chronic obstructive pulmonary disorder, inflammation associated with burns, lung injury, osteoarthritis, atopic dermatitis, chronic urticaria, ischemia-reperfusion injury, acute respiratory distress syndrome, systemic inflammatory response syndrome, multiple organ dysfunction syndrome, Uveitis, tissue graft rejection, hyperacute rejection of transplanted organs, myocardial infarction, coronary thrombosis, vascular occlusion, post-surgical vascular reocclusion, artherosclerosis, polypoidal choroidal vasculopathy, traumatic central nervous system injury, ischemic heart disease, rheumatoid arthritis, systemic lupus erythematosus, Guillain-Barre syndrome, pancreatitis, lupus nephritis, lupus glomerulonephritis, psoriasis, Crohn's disease, vasculitis, ANCA vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome, immuno vasculitis, Graft versus host disease, Paroxysmal nocturnal hemoglobinuria, Sjoegrens syndrome, insulin-dependent diabetes, mellitus, lupus nephropathy, Heyman nephritis, membranous nephritis, glomerulonephritis, IGA nephropathy, Membranoproliferative glomerulonephritis, Antiphospholipid syndrome, Age related macular degeneration; Dry age related macular degeneration, Wet age related macular degeneration, Motor neurone disease, contact sensitivity responses, and inflammation resulting from contact of blood with artificial surfaces.

In some embodiments, the disease or disorder is selected from the group consisting of neutropenia, neutrophilia, C3-glomerulopathy, C3-glomerulonephritis, dense deposit disease, membranoproliferative glomerulonephritis, Kawasaki disease, Hemolytic uremic syndrome, atypical hemolytic uremic syndrome (aHUS), tissue graft rejection, hyperacute rejection of transplanted organs, rheumatoid arthritis, systemic lupus erythematosus, lupus nephritis, lupus glomerulonephritis, vasculitis, ANCA vasculitis, autoimmune hemolytic and thrombocytopenic states, immuno vasculitis, Graft versus host disease, lupus nephropathy, Heyman nephritis, membranous nephritis, glomerulonephritis, IGA nephropathy, Membranoproliferative and glomerulonephritis.

In some embodiments, the disease or disorder is selected from the group consisting of melanoma, lung cancer, lymphoma, sarcoma, carcinoma, fibrosarcoma, liposarcoma, chondrosarcoma, osteogenic sarcoma, angiosarcoma, lymphangiosarcoma, synovioma, mesothelioma, meningioma, leukemia, lymphoma, leiomyosarcoma, rhabdomyosarcoma, squamous cell carcinoma, basal cell carcinoma, adenocarcinoma, papillary carcinoma, cystadenocarcinoma, bronchogenic carcinoma, renal cell carcinoma, hepatocellular carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma. In some embodiments, the disease or disorder is selected from the group consisting of glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, and carcinoma.

In some embodiments, the method of treating further comprises administering to the human a therapeutically effective amount of one or more additional therapeutic agents. In some embodiments, the one or more additional therapeutic agents is selected from the group consisting of corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, CCR5 chemokine antagonists, CCR2 chemokine antagonists, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, CXCR1 chemokine antagonists, CXCR4 chemokine antagonists, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, and T cell receptor antagonists, and combinations thereof. In some embodiments, the one or more additional therapeutic agent is selected from the group consisting of Mannan-binding lectin serine protease-2 (MASP-2) inhibitors, Factor B inhibitors, Factor D inhibitors.

In some embodiments, the one or more additional therapeutic agent is selected from the group consisting of inhibitors of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO), and agonists of OX40, GITR, 4-1BB, ICOS, STING or CD40.

In some embodiments, the one or more additional therapeutic agent is selected from the group consisting of modulators of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX3CR1, and ChemR23.

In some embodiments, the one or more additional therapeutic agent is selected from the group consisting of corticosteroids, steroids, CD20 inhibitors and immunosuppressants. In some embodiments, the one or more additional therapeutic agent is an immunosuppressant. In some embodiments, the one or more additional therapeutic agent is a corticosteroid or steroid. In some embodiments, the one or more additional therapeutic agent is a CD20 inhibitor. In some embodiments, the one or more additional therapeutic agent is a corticosteroid or steroid and an immunosuppressant or a CD20 inhibitor. In some embodiments, the one or more additional therapeutic agent is a corticosteroid or steroid and an immunosuppressant. In some embodiments, the one or more additional therapeutic agent is a corticosteroid or steroid and a CD20 inhibitor.

In some embodiments, the one or more additional therapeutic agents is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, and LT-1951. In some embodiments, the one or more additional therapeutic agent is selected from the group consisting of OMS721, ALN-CC5, ACH-4471, AMY-101, Acthar gel, CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, KY-1003, CA-327 and CD4+CD25+ regulatory T-cells, and combinations thereof.

In some embodiments, the one or more additional therapeutic agent is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate.

In some embodiments, the one or more additional therapeutic agent is rituximab or cyclophosphamide. In some embodiments, the one or more additional therapeutic agent is rituximab. In some embodiments, the one or more additional therapeutic agent is cyclophosphamide. In some embodiments, the one or more additional therapeutic agent is prednisone. In some embodiments, the one or more additional therapeutic agent is rituximab or cyclophosphamide and prednisone.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In some embodiments, the compound(s) of the disclosure are administered to a patient (e.g., a human) intravenously, orally or topically. In a preferred embodiment, the compound(s) of the disclosure are preferably administered to a patient (e.g., a human) intravenously. The effective amount may be an amount sufficient to modulate C5a receptor activity and/or an amount sufficient to reduce or alleviate the symptoms presented by the patient. Preferably, the amount administered is sufficient to yield a plasma concentration of its active metabolite high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of the compounds of this disclosure that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravenously, intramuscularly, or subcutaneously, it is preferred that sufficient amount of the compound be administered to achieve a serum concentration of 5 ng (nanograms)/mL-10 μg (micrograms)/mL serum, more preferably sufficient compound to achieve a serum concentration of 20 ng-1 μg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Kits and Packages

The terms "kit" and "pharmaceutical kit" refer to a commercial kit or package comprising, in one or more suitable containers, one or more pharmaceutical compositions and instructions for their use. In one embodiment, kits comprising a compound of the present disclosure, or a pharmaceutically acceptable salt thereof, and instructions for its administration are provided. In one embodiment, kits comprising a compound of the present dis, or a pharmaceutically acceptable salt thereof, in combination with one or more (e.g., one, two, three, one or two, or one to three) additional therapeutic agents and instructions for their administration are provided.

In one embodiment, the compounds of this disclosure are formulated into administration units which are packaged in a single packaging. The single packaging encompasses but is not limited to a bottle, a child-resistant bottle, an ampoule, and a tube. In one embodiment, the compounds of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

V. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the disclosure:
EtOH: Ethanol
EtONa: Sodium ethoxide
THF: Tetrahydrofuran
TLC: Thin layer chromatography
MeOH: Methanol Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of (2R,3S)-2-[4-[cyclopentyl-[2-(dimethylamino)acetyl]amino]phenyl]-1-(2-fluoro-6-methyl-benzoyl)-N-[4-methyl-3-(trifluoromethyl)phenyl]piperidine-3-carboxamide

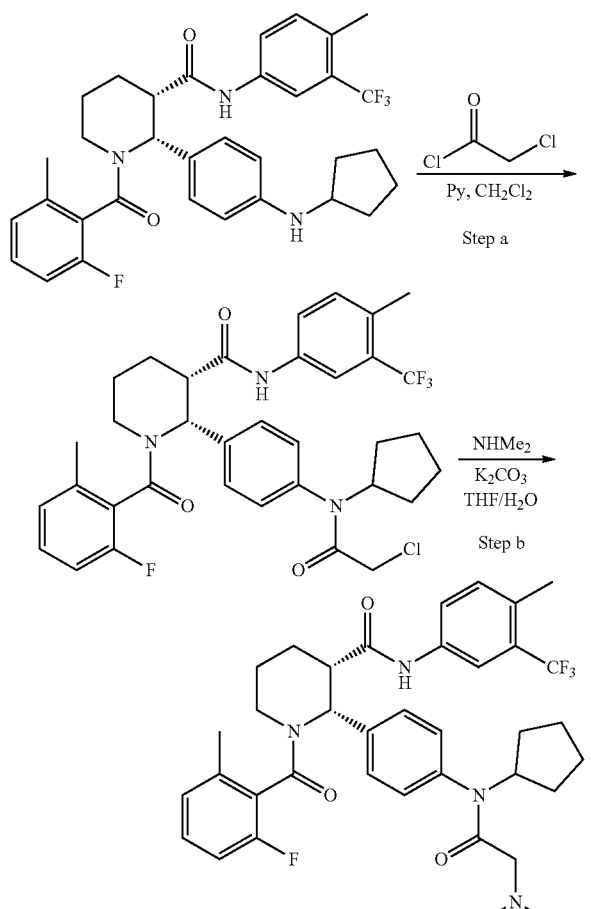

Step a: To a stirred solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (100 mg, 0.17 mmol) in anhydrous dichloromethane (5 mL) were added pyridine (0.2 mL, 0.26 mmol) and 2-chloroacetyl chloride (100 μL, 0.34 mmol) at room temperature. The mixture was stirred at room temperature for 1 h. After completion of the reaction, the reaction mixture was diluted with $CH_2Cl_2$, washed with 1N HCl, and then with saturated aqueous $NaHCO_3$ solution, dried over $Na_2SO_4$ and concentrated in vacuo. The crude was used directly in the next step without any further purification.

Step b: The crude product from above reaction was dissolved in tetrohydrofuran (5 mL) and $H_2O$ (1 mL), followed by adding $K_2CO_3$ (50 mg, 0.36 mmol) and 1M dimethylamine in THF (0.6 mL, 0.6 mmol). The mixture was then stirred at rt for overnight and then 60° C. for 2 h. After completion of the reaction, diluted with EtOAc, washed with water and dried over $Na_2SO_4$ and concentrated in vacuo. The crude compound was purified by silica gel chromatography (10-100% ethyl acetate/hexane first and then 0-15% MeOH/EtOAc) to give (2R,3S)-2-[4-[cyclopentyl-[2-(dimethylamino)acetyl]amino]phenyl]-1-(2-fluoro-6-methyl-benzoyl)-N-[4-methyl-3-(trifluoromethyl)phenyl]piperidine-3-carboxamide. MS: (ES) m/z calculated for $C_{37}H_{42}F_4N_4O_3[M+H]^+$ 667.3, found 667.8.

Example 2: Synthesis of (2R,3S)-2-[4-[(2-aminoacetyl)-cyclopentyl-amino]phenyl]-1-(2-fluoro-6-methyl-benzoyl)-N-[4-methyl-3-(trifluoromethyl)phenyl]piperidine-3-carboxamide

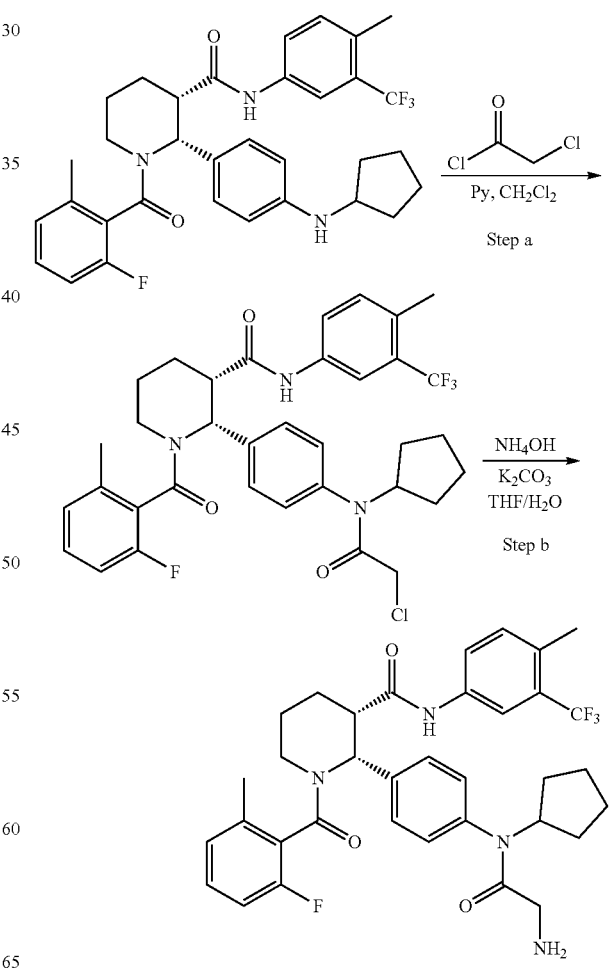

Same procedure as Example 1 except NH₄OH was used instead of dimethylamine in step b. The crude compound was purified by silica gel chromatography (10-100% ethyl acetate/hexane first and then 0-15% MeOH/EtOAc) to give (2R,3S)-2-[4-[(2-aminoacetyl)-cyclopentyl-amino]phenyl]-1-(2-fluoro-6-methyl-benzoyl)-N-[4-methyl-3-(trifluoromethyl)phenyl]piperidine-3-carboxamide. MS: (ES) m/z calculated for $C_{35}H_{38}F_4N_4O_3[M+H]^+$ 638.3, found 638.8.

Example 3: Synthesis of 2-[[[N-cyclopentyl-4-[(2R,3S)-1-(2-fluoro-6-methyl-benzoyl)-3-[[4-methyl-3-(trifluoromethyl)phenyl]carbamoyl]-2-piperidyl]anilino]-hydroxy-phosphoryl]amino]-3-(1H-imidazol-4-yl)propanoic acid

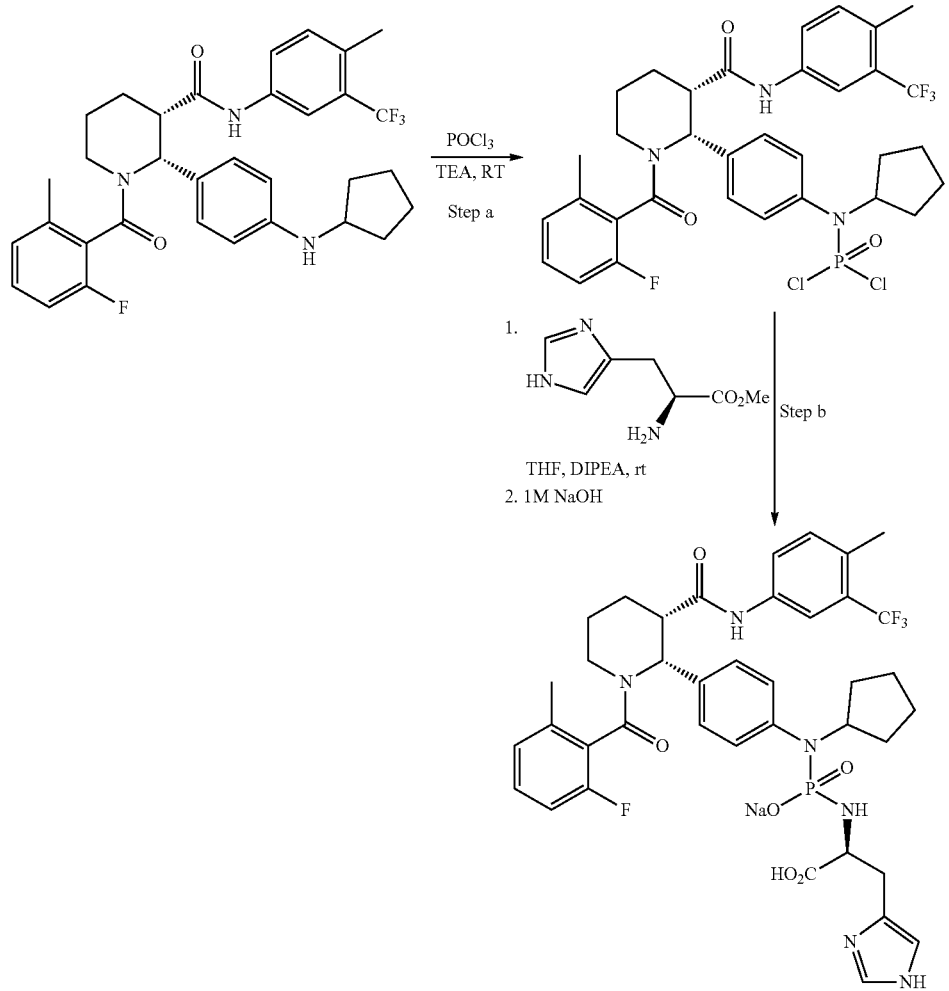

Step a: To a stirred solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (1.0 g, 1.78 mmol) in triethylamine (3.0 mL) was added POCl₃ (2.61 g, 17.8 mmol) at 0° C. The reaction mixture was stirred at 0° C. for 2 h and then allowed to warm to room temperature and stirred for 36 h. After completion of the reaction, it was quenched with ice at 0° C., stirred for 1 h and filtered. The crude compound was purified by silica gel chromatography (5-60% ethyl acetate/hexane) to give (2R,3S)-2-[4-[cyclopentyl(dichlorophosphoryl)-amino]phenyl]-1-(2-fluoro-6-methyl-benzoyl)-N-[4-methyl-3-(trifluoromethyl)phenyl]-piperidine-3-carboxamide the desired product. MS: (ES) m/z calculated for $C_{33}H_{34}Cl_2F_4N_3O_3P$ $[M+H]^+$ 698.1, found 698.6.

Step b: To a stirred solution of (2R,3S)-2-[4-[cyclopentyl(dichlorophosphoryl)amino]phenyl]-1-(2-fluoro-6-methyl-benzoyl)-N-[4-methyl-3-(trifluoromethyl)phenyl]piperidine-3-carboxamide (250 mg, 0.36 mmol) in anhydrous THF (4 mL) was added methyl (2S)-2-amino-3-(1H-imidazol-4-yl)propanoate (216 mg, 0.89 mmol) and N,N-diisopropyl ethylamine (231 mg, 1.79 mmol). The mixture was stirred at room temperature for overnight. After completion of the reaction, water (2 mL) was added and stirred for 2 h. The reaction mixture was then extracted with EtOAc, washed with brine, dried over Na₂SO₄ and concentrated in vacuo. The crude product was purified by silica gel chromatography (0-100% EtOAc/hexane) give the free acid which was then treated with 1N NaOH (1 equiv.) and lyophilized to obtain 2-[[[N-cyclopentyl-4-[(2R,3S)-1-(2-fluoro-6-methyl-benzoyl)-3-[[4-methyl-3-(trifluoromethyl)phenyl]carbamoyl]-2-piperidyl]anilino]-hydroxy-phosphoryl]amino]-3-(1H-imidazol-4-yl)propanoic acid. MS: (ES) m/z calculated for $C_{39}H_{43}F_4N_6O_6P[M+H]^+$ 799.3, found 799.7.

Example 4: Synthesis of N-cyclopentyl-N-[4-[(2R,3S)-1-(2-fluoro-6-methyl-benzoyl)-3-[[4-methyl-3 (trifluoromethyl)phenyl]carbamoyl]-2-piperidyl]phenyl]-(2-methylpropanoyloxy)phosphonamidic acid

Example 5: Synthesis of (2R,3S)-2-[4-[[2-[(2-aminoacetyl)amino]acetyl]-cyclopentyl-amino]phenyl]-1-(2-fluoro-6-methyl-benzoyl)-N-[4-methyl-3-(trifluoromethyl)phenyl]piperidine-3-carboxamide

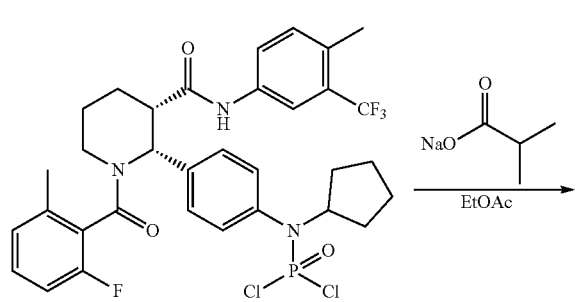

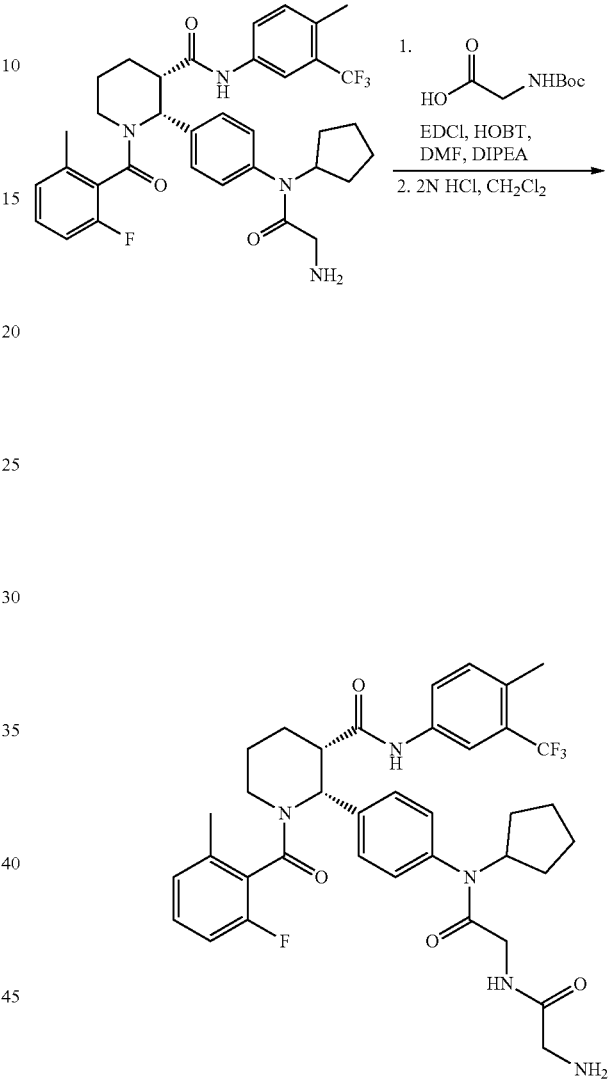

To a stirred solution of (2R,3S)-2-[4-[cyclopentyl(dichlorophosphoryl)amino]phenyl]-1-(2-fluoro-6-methyl-benzoyl)-N-[4-methyl-3-(trifluoromethyl)phenyl]piperidine-3-carboxamide (200 mg, 0.28 mmol, see Example 3) in ethyl acetate (4 mL) was added sodium salt of isobutyric acid (85 mg, 0.72 mmol). The reaction mixture was stirred at room temperature for overnight. After completion of the reaction, saturated aqueous NH$_4$Cl solution was added, extracted with EtOAc, concentrated in vacuo. The crude product was purified by silica gel chromatography (0-20% MeOH/CH$_2$Cl$_2$) to give N-cyclopentyl-N-[4-[(2R,3S)-1-(2-fluoro-6-methyl-benzoyl)-3-[[4-methyl-3 (trifluoromethyl)phenyl]carbamoyl]-2-piperidyl]phenyl]-(2-methylpropanoyloxy) phosphonamidic acid. MS: (ES) m/z calculated for C$_{37}$H$_{42}$F$_4$N$_3$O$_6$P[M+H]$^+$ 732.3, found 732.3.

(2R,3S)-2-[4-[(2-Aminoacetyl)-cyclopentyl-amino]phenyl]-1-(2-fluoro-6-methyl-benzoyl)-N-[4-methyl-3-(trifluoromethyl)phenyl]piperidine-3-carboxamide (200 mg, 0.31 mmol), 2-(tert-butoxycarbonylamino)acetic acid (82 mg, 0.46 mmol), EDCI (118 mg, 0.62 mmol), HOBT (71 mg, 0.46 mmol) and DIPEA (99 mg, 0.77 mmol) were added into a vial with DMF (2 mL). The reaction mixture was stirred at room temperature for 24 h. After completion of the reaction, the reaction mixture was diluted with EtOAc, washed with saturated aqueous NaHCO$_3$ solution and water, dried over Na$_2$SO$_4$ and concentrated in vacuo. The crude product was purified by silica gel chromatography (10-100% EtOAc/hexane). The desired material was then dissolved in CH$_2$Cl$_2$ (3 mL) and treated with 2N HCl in dioxane (2 mL) at rt for 2 h. After completion of the reaction, the solvent was removed and the residue was diluted with CH$_2$Cl$_2$ and washed with saturated aqueous NaHCO$_3$ solution and water, dried over Na$_2$SO$_4$ and concentrated in vacuo. The crude product was purified by silica gel chromatography (0-20% MeOH/CH$_2$Cl$_2$) to give the (2R,3S)-2-[4-[[2-[(2-aminoacetyl)amino]acetyl]-cyclopentyl-amino]phenyl]-1-(2-fluoro-6-methyl-benzoyl)-N-[4-methyl-3-(trifluoromethyl)phenyl]piperidine-3-carboxamide. MS: (ES) m/z calculated for C$_{37}$H$_{41}$F$_4$N$_5$O$_4$[M+H]$^+$ 696.3, found 696.7.

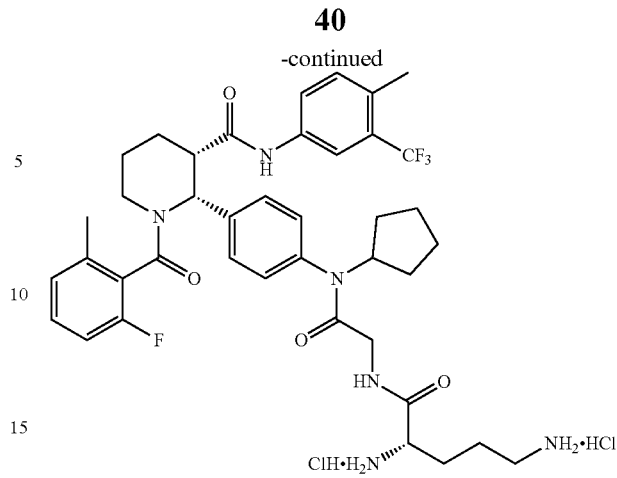

(2R,3S)-2-[4-[(2-Aminoacetyl)-cyclopentyl-amino]phenyl]-1-(2-fluoro-6-methyl-benzoyl)-N-[4-methyl-3-(trifluoromethyl)phenyl]piperidine-3-carboxamide (250 mg, 0.39 mmol), (2S)-2,5-bis(tert-butoxycarbonylamino)pentanoic acid (309 mg, 0.59 mmol), EDCI (150 mg, 0.78 mmol), HOBT (90 mg, 0.59 mmol) and DIPEA (151 mg, 1.17 mmol) were added into a vial with DMF (3.0 mL). The reaction was stirred at room temperature for 24 h. After completion of the reaction, diluted with EtOAc, washed with water, dried over Na$_2$SO$_4$ and concentrated in vacuo. The crude product was purified by silica gel chromatography (10-100% EtOAc/hexane first, then 0-20% MeOH/CH$_2$Cl$_2$). The product was then dissolved in CH$_2$Cl$_2$ (3 mL) and treated with 2N HCl in dioxane (2 mL) at rt for 2 h. After completion of the reaction, the solvent was removed and the residue was triturated with CH$_3$CN to give the (2R,3S)-2-[4-[cyclopentyl-[2-[[(2S)-2,5-diaminopentanoyl]amino]acetyl]amino]phenyl]-1-(2-fluoro-6-methyl-benzoyl)-N-[4-methyl-3-(trifluoromethyl)phenyl]piperidine-3-carboxamide dihydrochloride. MS: (ES) m/z calculated for C$_{40}$H$_{48}$F$_4$N$_6$O$_4$[M+H]$^+$ 752.4, found 752.4.

Example 6: Synthesis of (2R,3S)-2-[4-[cyclopentyl-[2-[[(2S)-2,5-diaminopentanoyl]amino]acetyl]amino]phenyl]-1-(2-fluoro-6-methyl-benzoyl)-N-[4-methyl-3-(trifluoromethyl)phenyl]piperidine-3-carboxamide dihydrochloride

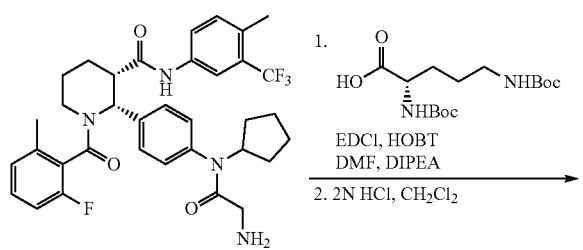

Example 7: Synthesis of [cyclopentyl-[4-[(2R,3S)-1-(2-fluoro-6-methyl-benzoyl)-3-[[4-methyl-3-(trifluoromethyl)phenyl]carbamoyl]-2-piperidyl]phenyl]carbamoyl]oxymethyl (2S)-2-amino-3-methyl-butanoate

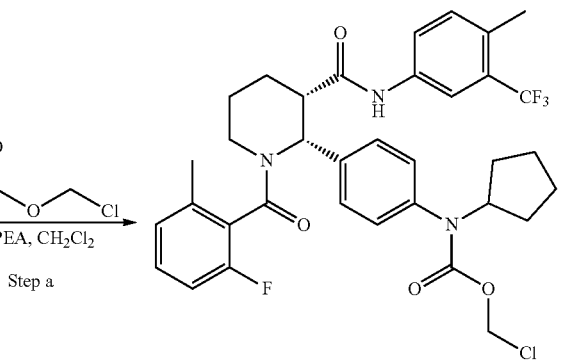

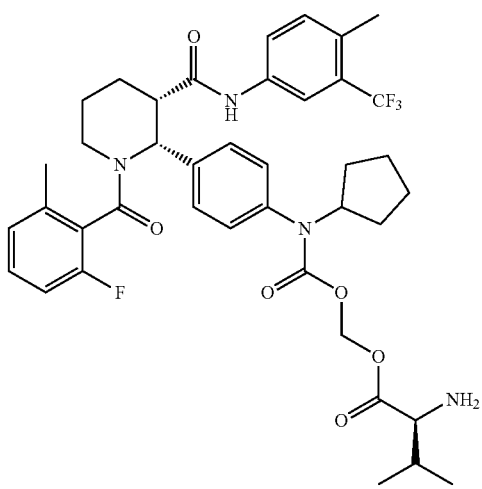
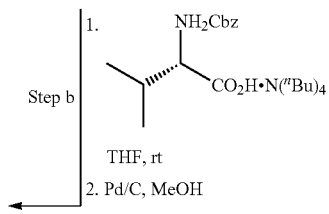

Step a: To a stirred solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (3.0 g, 5.15 mmol) in anhydrous dichloromethane (25 mL) were added DIPEA (997 mg, 7072 mmol) and chloromethyl carbonochloridate (791 mg, 6.02 mmol) at 0° C. The mixture was stirred for 2 h. After completion of the reaction, the reaction was quenched with water, extracted with $CH_2Cl_2$ and obtained crude product chloromethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate (3.5 g, yield: 100%). MS: (ES) m/z calculated for $C_{35}H_{36}ClF_4N_3O_4[M+H]^+$ 674.2, found 674.5.

Step b: To a stirred solution of chloromethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate (450 mg, 0.67 mmol) in anhydrous THF (5.0 mL) at room temperature was added the adduct obtained from (2S)-2-(benzyloxycarbonylamino)-3-methyl-butanoic acid (251 mg, 1 mmol) and tetrabutylammonium hydroxide (260 mg, 1 mmol) mixing and lyophilization. The reaction was stirred at room temperature for 48 h. After completion of the reaction, the mixture was quenched with water, extracted with EtOAc and purified by silica gel chromatography (10-50% ethyl acetate/hexane) to give the desired intermediate. It was then hydrogenated in methanol using palladium on carbon as catalyst to give the desired product, [cyclopentyl-[4-[(2R,3S)-1-(2-fluoro-6-methyl-benzoyl)-3-[[4-methyl-3-(trifluoromethyl)phenyl]carbamoyl]-2-piperidyl]phenyl]carbamoyl]oxymethyl (2S)-2-amino-3-methyl-butanoate. MS: (ES) m/z calculated for $C_{40}H_{46}F_4N_4O_6[M+H]^+$ 755.3, found 755.5.

Example 8: Synthesis of (4-phosphonooxyphenyl)methyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate

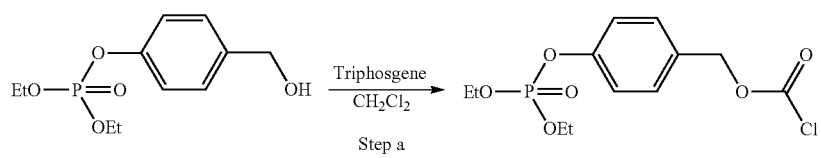

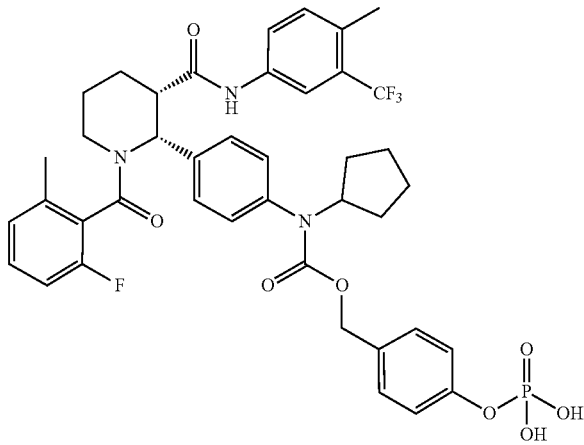

Step a: To a stirred solution of diethyl [4-(hydroxymethyl)phenyl]phosphate (0.3 g, 1.14 mmol) in anhydrous dichloromethane (4 mL) was added triphosgene (0.67 g, 2.29 mmol) at rt and stirred for 4 h. Then the solvent was removed and dried under vacuum for 30 min. The obtained residue was used directly in the next step.

Step b: Above residue was added to the solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (0.66 g, 1.13 mmol) and N,N-diisopropylethylamine (598 mg, 4.63 mmol) in dichloromethane (5 mL). The reaction mixture was stirred at room temperature for overnight. After completion of the reaction, it was worked up by water wash, and extracted with CH$_2$Cl$_2$. The crude product was purified by silica gel chromatography (20-100% ethyl acetate/hexane) to give the desired intermediate. This intermediate (80 mg) was then dissolved in CH$_2$Cl$_2$ (1 mL) and treated with bromotrimethylsilane (84 mg, 0.55 mmol) at room temperature for overnight. After completion of the reaction, the reaction mixture was concentrated to dryness and purified by preparative HPLC (acetonitrile-water with 0.1% TFA) to give (4-phosphonooxyphenyl)methyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate. MS: (ES) m/z calculated for C$_{41}$H$_{42}$F$_4$N$_3$O$_8$P[M+H]$^+$ 812.3, found 812.4.

Example 9: Synthesis of Disodium Salt of phosphonooxymethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate

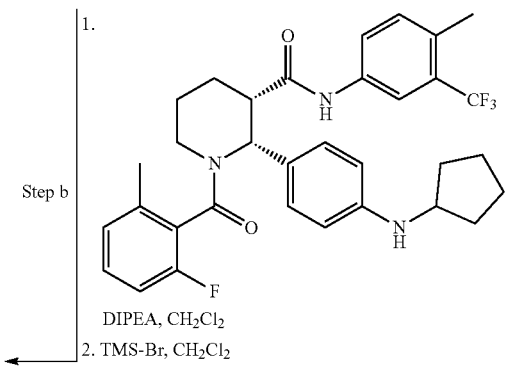

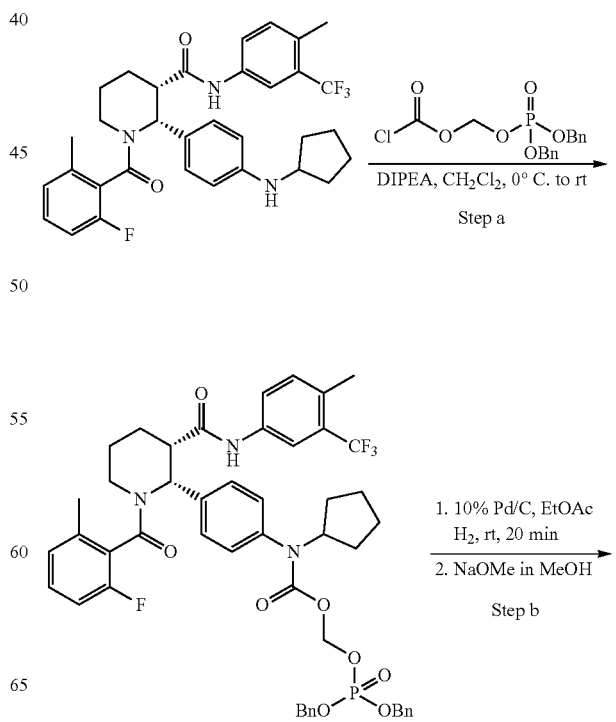

-continued

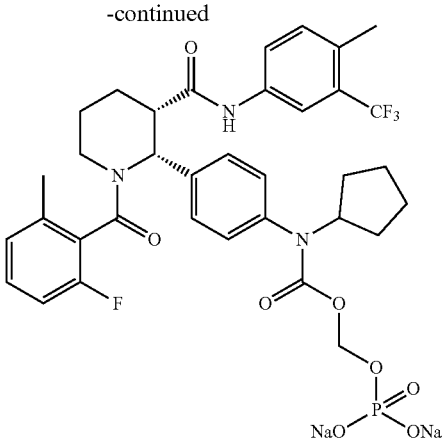

Step a: To a stirred solution of dibenzyloxyphosphoryloxymethyl carbonochloridate (526 mg, (~60% pure, 1.05 g, prepared as described in WO 2014/193696), 1.42 mmol) in anhydrous dichloromethane (10 mL) were added DIPEA (1.3 mL, 7.1 mmol) at 0° C. Then a solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (826 mg, 1.42 mmol) in anhydrous dichloromethane (5 mL) was added at 0° C. The mixture was stirred for 2 h. After completion of the reaction, the reaction was quenched with water, extracted with $CH_2Cl_2$, dried over $Mg_2SO_4$ and concentrated in vacuo. The crude product was purified by silica gel chromatography (20-100% EtOAc/hexane) to give the desired product, dibenzyloxyphosphoryloxymethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate. MS: (ES) m/z calculated for $C_{49}H_{50}F_4N_3O_8P[M+H]^+$ 916.6, found 916.6.

Step b: To a solution of dibenzyloxyphosphoryloxymethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate (690 mg, 0.75 mmol) in ethyl acetate (15 mL) was added palladium on carbon (2 g, 10% by wt), hydrogenated under 60 psi for 20 min, filtered through Celite, rinsed with 1:1 EtOAc/MeOH (15 mL), concentrated to dryness. The residue was dissolved in MeOH and treated with 1M NaOMe (1.57 mL, 1.57 mmol). The mixture was concentrated in vacuo to dryness and added solvent ether, then filtered and rinsed with solvent ether to give disodium salt of phosphonooxymethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate, MS: (ES) m/z calculated for $C_{35}H_{38}F_4N_3O_8P[M+H]^+$ 736.6, found 736.6.

Example 10: Synthesis of Sodium Salt of (E)-4-[[cyclopentyl-[4-[(2R,3S)-1-(2-fluoro-6-methyl-benzoyl)-3-[[4-methyl-3-(trifluoromethyl)phenyl]carbamoyl]-2-piperidyl]phenyl]carbamoyl]oxymethoxy]-4-oxo-but-2-enoic acid

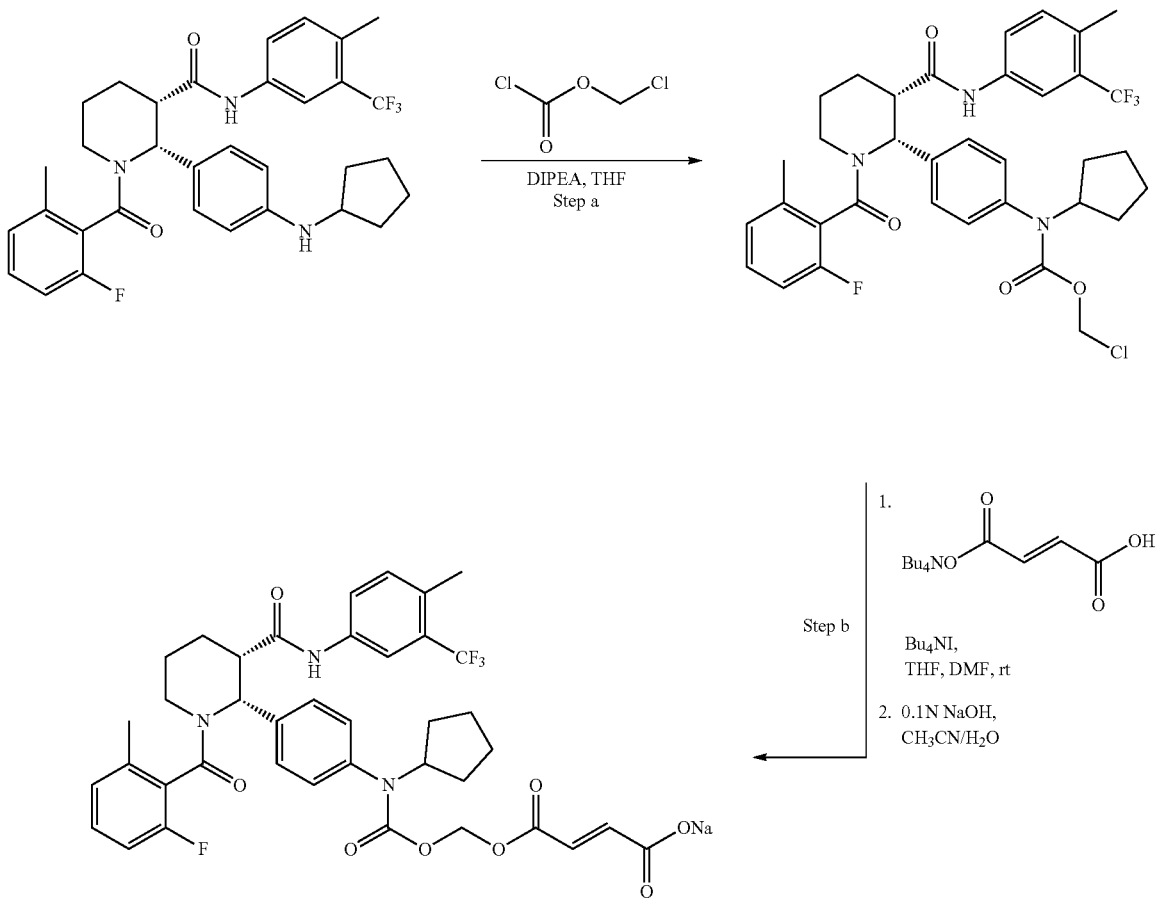

Step a: To a stirred solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (1 g, 1.72 mmol) in anhydrous THF (10 mL) was added chloromethyl carbonochloridate (155 µL, 1.72 mmol) and N,N-diisopropylethylamine (392 µL, 2.58 mmol) at 0° C. for 1 h. After completion of the reaction, the solvent was removed and obtained chloromethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl] carbamate.

Step b: To the solution of chloromethyl N-cyclopentyl-N-[4-[(2R,3S)-1-(2-fluoro-6-methyl-benzoyl)-3-[[4-methyl-3-(trifluoromethyl)phenyl]carbamoyl]-2-piperidyl]phenyl]carbamate (200 mg, 0.297 mmol) and fumaric acid tetrabutylammonium salt (106 mg, 0.297 mmol) in THF (5 mL) was added tetrabutylamonium iodide (22 mg, 0.06 mmol) in DMF at rt. The mixture was stirred for overnight, then diluted with EtOAc, washed with 0.1 M HCl, dried over $Na_2SO_4$ and concentrated in vacuo. The crude was purified by silica gel chromatography 5-10% $MeOH/CH_2Cl_2$. The collected product was converted to sodium salt by diluting with $CH_3CN$ (0.6 mL)/$H_2O$ (0.4 mL) and adding 0.1 M NaOH (213 µL, 1 equiv.). Lyophilized and obtained sodium salt of (E)-4-[[cyclopentyl-[4-[(2R,3S)-1-(2-fluoro-6-methyl-benzoyl)-3-[[4-methyl-3-(trifluoromethyl)phenyl]carbamoyl]-2-piperidyl]phenyl]carbamoyl]oxymethoxy]-4-oxo-but-2-enoic acid. MS: (ES) m/z calculated for $C_{39}H_{38}F_4N_3O_8[M+H]^+$ 754.2, found 754.7.

Example 11: Synthesis of disodium salt of [N-[(2R,3S)-2-[4-(cyclopentylamino)phenyl]-1-(2-fluoro-6-methyl-benzoyl)piperidine-3-carbonyl]-4-methyl-3-(trifluoromethyl)anilino]methyl dihydrogen phosphate

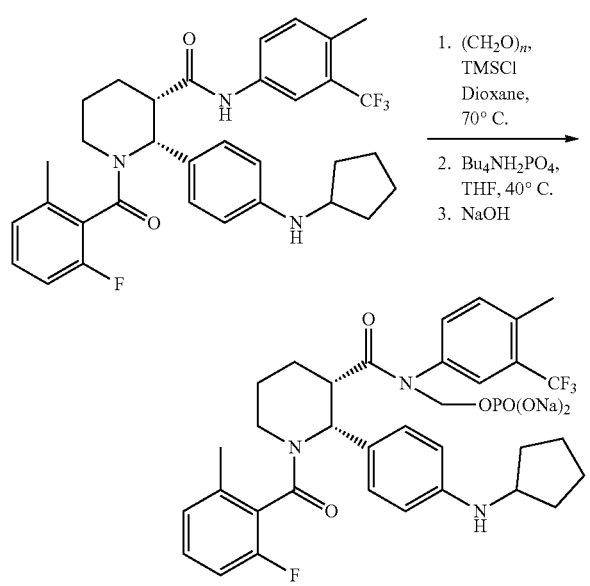

To a suspension of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (1.99 g, 3.42 mmol) and paraformaldehyde (308 mg, 10.26 mmol) in dioxane (10 mL) was added chlorotrimethylsilane (20 mL, 157.58 mmol) and warmed up to 70° C. The reaction was stirred for 9 h and then concentrated in vacuo. The residue was dissolved in THF (10 mL) and added tetrabutylammonium dihydrogen phosphate (3.7 g, 10.9 mmol). The mixture was stirred at 40° C. for 1 h, then treated with ammonium hydroxide (5 mL), water (20 mL) and $CH_2Cl_2$ (30 mL). The organic layer was concentrated in vacuo and purified by silica gel chromatography (3-60% ($MeOH:NH_4OH$ 4:1/vol)/$CH_2Cl_2$ first. Then it was purified by preparative HPLC (acetonitrile-water with 0.1% $NH_4HCO_3$/ACN). The desired fractions were collected and concentrated in vacuo. The residue was then treated with 2 mL $H_2O$, 1 mL $CH_3CN$ and 1N NaOH (137 µL, 2 equiv.), lyophilized and obtained disodium salt of [N-[(2R,3S)-2-[4-(cyclopentylamino)phenyl]-1-(2-fluoro-6-methyl-benzoyl)piperidine-3-carbonyl]-4-methyl-3-(trifluoromethyl)anilino]methyl dihydrogen phosphate, MS: (ES) m/z calculated for $C_{34}H_{38}F_4N_3O_6P$ $[M+H]^+$692.2, found 692.6.

Example 12: Synthesis of [N-[(2R,3S)-2-[4-(cyclopentylamino)phenyl]-1-(2-fluoro-6-methyl-benzoyl)piperidine-3-carbonyl]-4-methyl-3-(trifluoromethyl)anilino]phosphonic acid

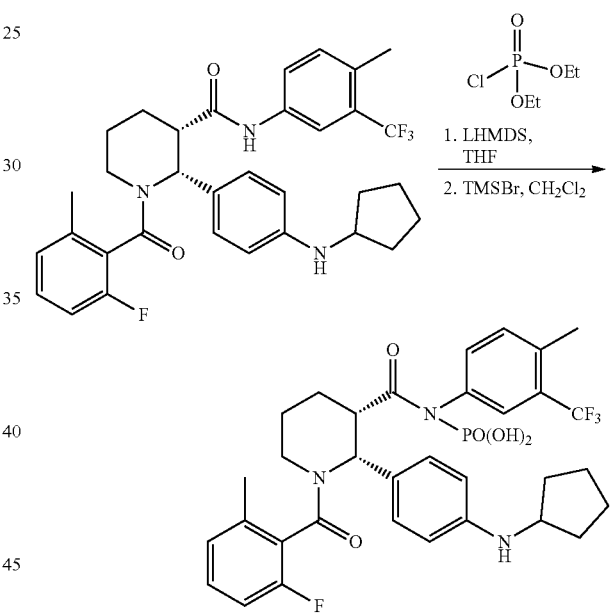

To a stirred solution of (2R,3S)-2-[4-(cyclopentylamino)phenyl]-1-(2-fluoro-6-methyl-benzoyl)-N-[4-methyl-3-(trifluoromethyl)phenyl]piperidine-3-carboxamide (291 mg, 0.50 mmol) in THF (3 mL) at −78° C. was added LHMDS (72 µL, 0.55 mmol). The mixture was stirred for 5 min. 1-[chloro(ethoxy)phosphoryl]oxyethane (72 µL, 0.50 mmol) was added and slowly warmed up to rt. At the completion of the reaction, it was diluted with EtOAc, washed with saturated $NaHCO_3$ solution, and extracted with EtOAc. The crude product was purified by silica gel chromatography (0-100% EtOAc/hexane) to yield 60 mg of desired intermediate. This intermediate was dissolved in $CH_2Cl_2$ (1 mL) and TMSBr (0.2 mL) was added at 0° C. The mixture was warmed up to rt and stirred for 2 h. It was then concentrated in vacuo and purified by preparative HPLC (acetonitrile-water with 0.1% TFA) to give [N-[(2R,3S)-2-[4-(cyclopentylamino)phenyl]-1-(2-fluoro-6-methyl-benzoyl)piperidine-3-carbonyl]-4-methyl-3-(trifluoromethyl)anilino] phosphonic acid. MS: (ES) m/z calculated for $C_{33}H_{36}F_4N_3O_5P[M+H]^+$662.3, found 662.3.

Example 13: Synthesis of ([4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-[(2-aminoacetyl)amino]acetate

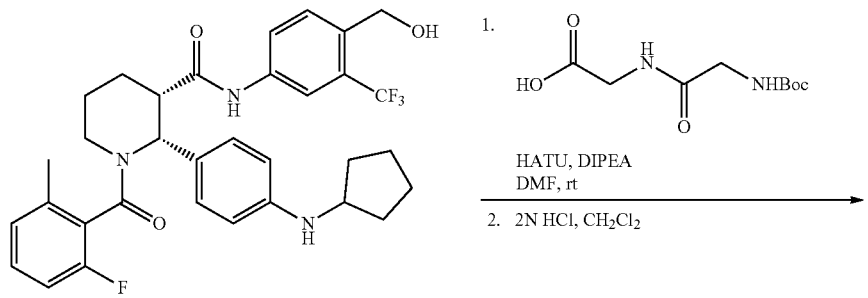

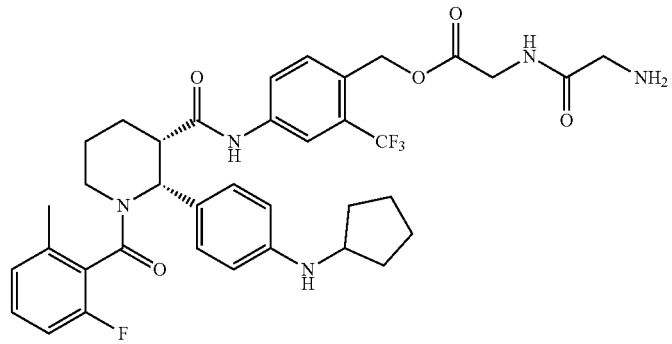

(2R,3S)-2-[4-(Cyclopentylamino)phenyl]-1-(2-fluoro-6-methyl-benzoyl)-N-[4-(hydroxymethyl)-3-(trifluoromethyl)phenyl]piperidine-3-carboxamide (220 mg, 0.37 mmol), 2-[[2-(tert-butoxycarbonylamino)acetyl]amino]acetic acid (213 mg, 0.92 mmol), HATU (210 mg, 0.55 mmol) and DIPEA (95 mg, 0.74 mmol) were added into a vial with DMF (2 mL). The reaction was stirred at 55° C. for 24 h. After completion of the reaction, the reaction mixture was diluted with EtOAc, washed with saturated aqueous NaHCO$_3$ solution and water, dried over Na$_2$SO$_4$ and concentrated in vacuo. The residue was then dissolved in CH$_2$Cl$_2$ (3 mL) and treated with 2N HCl in dioxane (2 mL) at rt for 2 h. After completion of the reaction, the solvent was removed and the residue was diluted with CH$_2$Cl$_2$ and washed with saturated aqueous NaHCO$_3$ solution and water, dried over Na$_2$SO$_4$ and concentrated in vacuo. The crude product was purified by silica gel chromatography (0-20% MeOH/CH$_2$Cl$_2$) to give ([4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-[(2-aminoacetyl)amino]acetate. MS: (ES) m/z calculated for C$_{37}$H$_{41}$F$_4$N$_5$O$_5$[M+H]$^+$ 712.3, found 712.7.

Example 14: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-[[(2S)-2-amino-3-methyl-butanoyl]amino]acetate

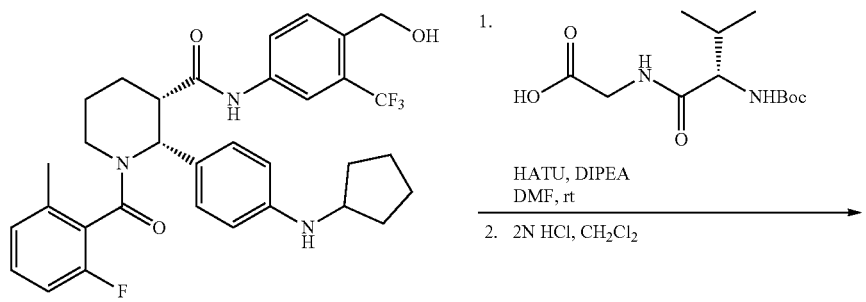

-continued

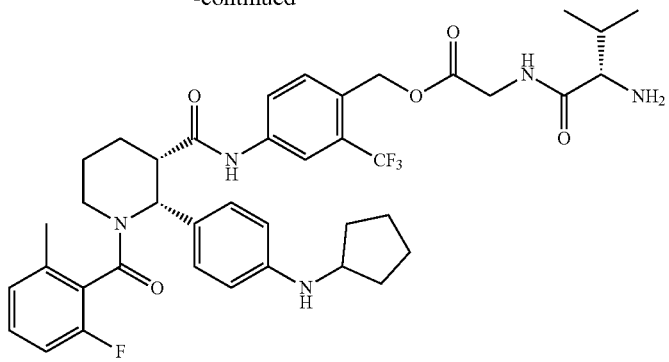

(2R,3S)-2-[4-(Cyclopentylamino)phenyl]-1-(2-fluoro-6-methyl-benzoyl)-N-[4-(hydroxymethyl)-3-(trifluoromethyl)phenyl]piperidine-3-carboxamide (200 mg, 0.33 mmol), 2-[[(2S)-2-(tert-butoxycarbonyl amino)-3-methyl-butanoyl]amino]acetic acid (138 mg, 0.50 mmol), HATU (190 mg, 0.50 mmol) and DIPEA (108 mg, 0.84 mmol) were added into a vial with DMF (2.0 mL). The same procedure as Example 1 was followed to give product [4-[[(2R,3S)-2-[4-(cyclopentylamino)phenyl]-1-(2-fluoro-6-methyl-benzoyl)piperidine-3-carbonyl]amino]-2-(trifluoromethyl)phenyl] methyl 2-[[(2S)-2-amino-3-methyl-butanoyl]amino]acetate. MS: (ES) m/z calculated for $C_{40}H_{47}F_4N_5O_5[M+H]^+$ 754.3, found 754.8.

Example 15: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-[(2-aminoacetyl)amino]-3-methyl-butanoate

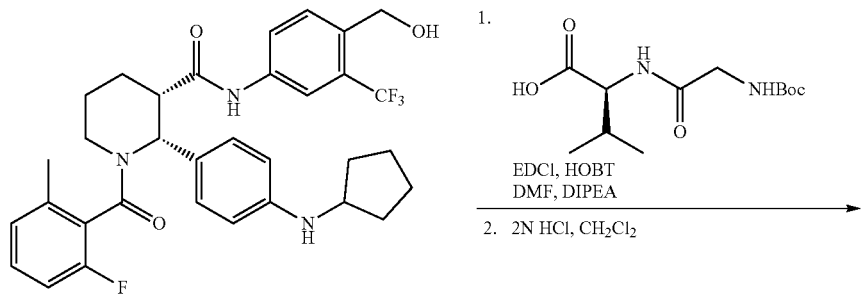

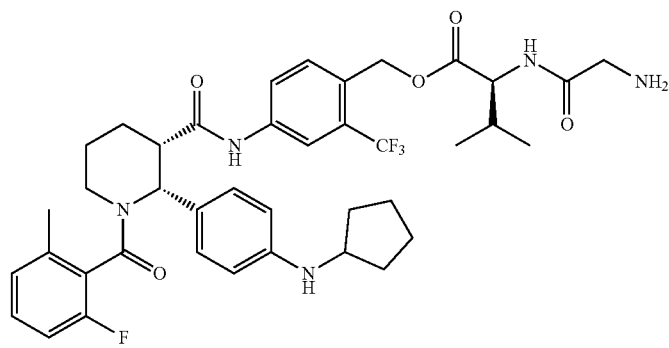

(2R,3S)-2-[4-(Cyclopentylamino)phenyl]-1-(2-fluoro-6-methyl-benzoyl)-N-[4-(hydroxymethyl)-3-(trifluoromethyl)phenyl]piperidine-3-carboxamide (250 mg, 0.42 mmol), (2S)-2-[[2-(tert-butoxycarbonylamino)acetyl]amino]-3-methyl-butanoic acid (172 mg, 0.62 mmol), EDCI (160 mg, 0.83 mmol), HOBT (96 mg, 0.62 mmol) and DIPEA (108 mg, 0.83 mmol) were added into a vial with DMF (2.5 mL). The reaction was stirred at room temperature for 24 h. After completion of the reaction, diluted with EtOAc, washed with water, dried over Na$_2$SO$_4$ and concentrated in vacuo. The crude product was purified by silica gel chromatography (10-100% EtOAc/hexane first, then 0-20% MeOH/CH$_2$Cl$_2$). The product was then dissolved in CH$_2$Cl$_2$ (3 mL) and treated with 2N HCl in dioxane (2 mL) at rt for 2 h. After completion of the reaction, the reaction was diluted with CH$_2$Cl$_2$ and washed with saturated NaHCO$_3$ and water, dried over Na$_2$SO$_4$ and concentrated in vacuo. The crude product was purified by silica gel chromatography (0-20% MeOH/CH$_2$Cl$_2$) to give product [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-[(2-aminoacetyl)amino]-3-methyl-butanoate. MS: (ES) m/z calculated for C$_{40}$H$_{47}$F$_4$N$_5$O$_5$[M+H]$^+$ 754.3, found 754.8.

Example 16: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-[[(2S)-2-amino-3-methyl-butanoyl]amino]-3-methyl-butanoate

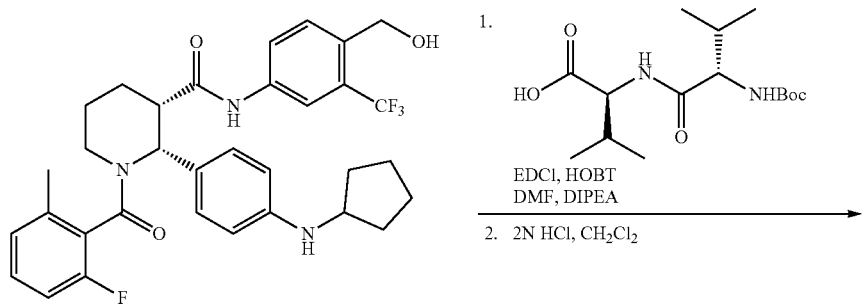

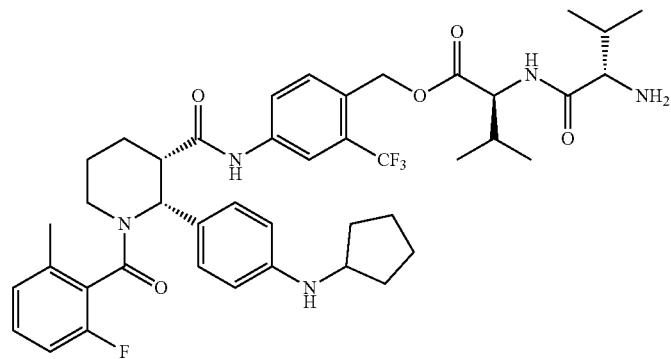

(2R,3S)-2-[4-(Cyclopentylamino)phenyl]-1-(2-fluoro-6-methyl-benzoyl)-N-[4-(hydroxymethyl)-3-(trifluoromethyl)phenyl]piperidine-3-carboxamide (250 mg, 0.42 mmol), (2S)-2-[[(2 S)-2-(tert-butoxycarbonylamino)-3-methyl-butanoyl]amino]-3-methyl-butanoic acid (196 mg, 0.62 mmol), EDCI (160 mg, 0.83 mmol), HOBT (96 mg, 0.62 mmol) and DIPEA (108 mg, 0.83 mmol) were added into a vial with DMF (2.0 mL). The same procedure as Example 3 was followed to give product [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-[[(2S)-2-amino-3-methyl-butanoyl]amino]-3-methyl-butanoate. MS: (ES) m/z calculated for $C_{43}H_{53}F_4N_5O_5$[M+H]$^+$ 796.4, found 796.8.

Example 17: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2R)-2-amino-3-methyl-butanoate

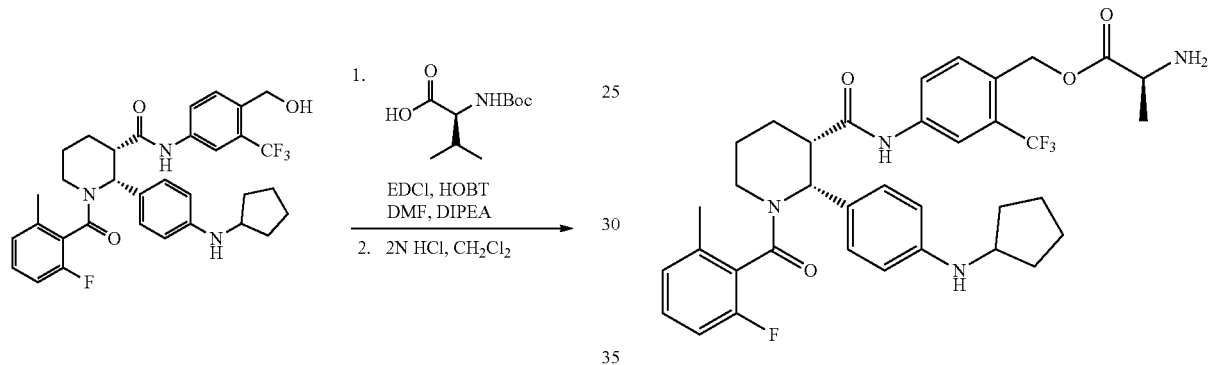

(2R,3S)-2-[4-(Cyclopentylamino)phenyl]-1-(2-fluoro-6-methyl-benzoyl)-N-[4-(hydroxymethyl)-3-(trifluoromethyl)phenyl]piperidine-3-carboxamide (250 mg, 0.42 mmol), (2S)-2-(tert-butoxycarbonylamino)-3-methyl-butanoic acid (180 mg, 0.83 mmol), EDCI (160 mg, 0.83 mmol), HOBT (96 mg, 0.62 mmol) and DIPEA (108 mg, 0.83 mmol) were added into a vial with DMF (4 mL). The same procedure as Example 3 was followed to give product [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-amino-3-methyl-butanoate. MS: (ES) m/z calculated for $C_{38}H_{44}F_4N_4O_4$[M+H]$^+$ 697.4, found 697.7.

Example 18: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-aminopropanoate

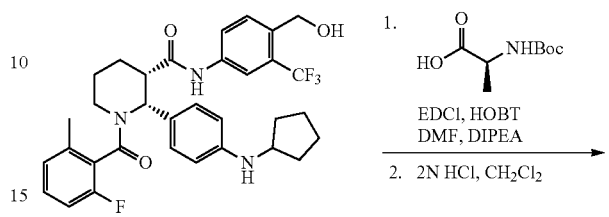

(2R,3S)-2-[4-(Cyclopentylamino)phenyl]-1-(2-fluoro-6-methyl-benzoyl)-N-[4-(hydroxymethyl)-3-(trifluoromethyl)phenyl]piperidine-3-carboxamide (250 mg, 0.42 mmol), (2S)-2-(tert-butoxycarbonylamino)propanoic acid (118 mg, 0.62 mmol), EDCI (119 mg, 0.83 mmol), HOBT (96 mg, 0.62 mmol) and DIPEA (134 mg, 1.04 mmol) were added into a vial with DMF (4.0 mL). The same procedure as Example 3 was followed to give product [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl (2S)-2-aminopropanoate. MS: (ES) m/z calculated for $C_{36}H_{40}F_4N_4O_4$[M+H]$^+$ 669.3, found 669.7.

Example 19: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-(dimethylamino)acetate

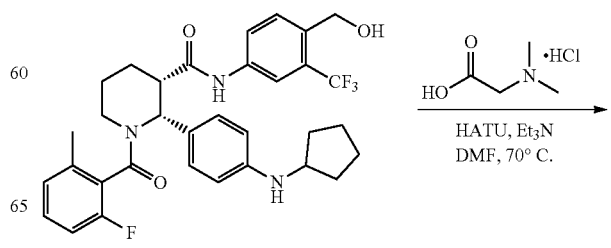

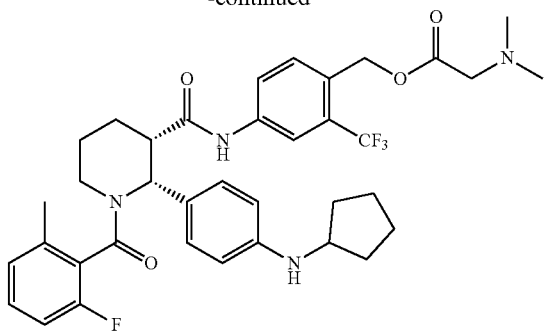

To a stirred solution of (2R,3S)-2-[4-(cyclopentylamino)phenyl]-1-(2-fluoro-6-methyl-benzoyl)-N-[4-(hydroxymethyl)-3-(trifluoromethyl)phenyl]piperidine-3-carboxamide (70 mg, 0.12 mmol) and 2-(dimethylamino)acetic acid hydrochloride (49 mg, 0.35 mmol) in DMF (2.5 mL) was added HATU (135 mg, 0.36 mmol) and triethylamine (82 μL, 0.59 mmol). The mixture was warmed to 70° C. and stirred for 2 h. It was then cooled to rt, diluted with EtOAc, washed with saturated aqueous NaHCO$_3$ solution and water, and concentrated in vacuo. The crude was purified by silica gel chromatography (0-100% EtOAc/hexane) to give [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-(dimethylamino)acetate, MS: (ES) m/z calculated for $C_{37}H_{42}F_4N_4O_4$[M+H]$^+$ 683.3, found 683.3.

Example 20: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-aminoacetate

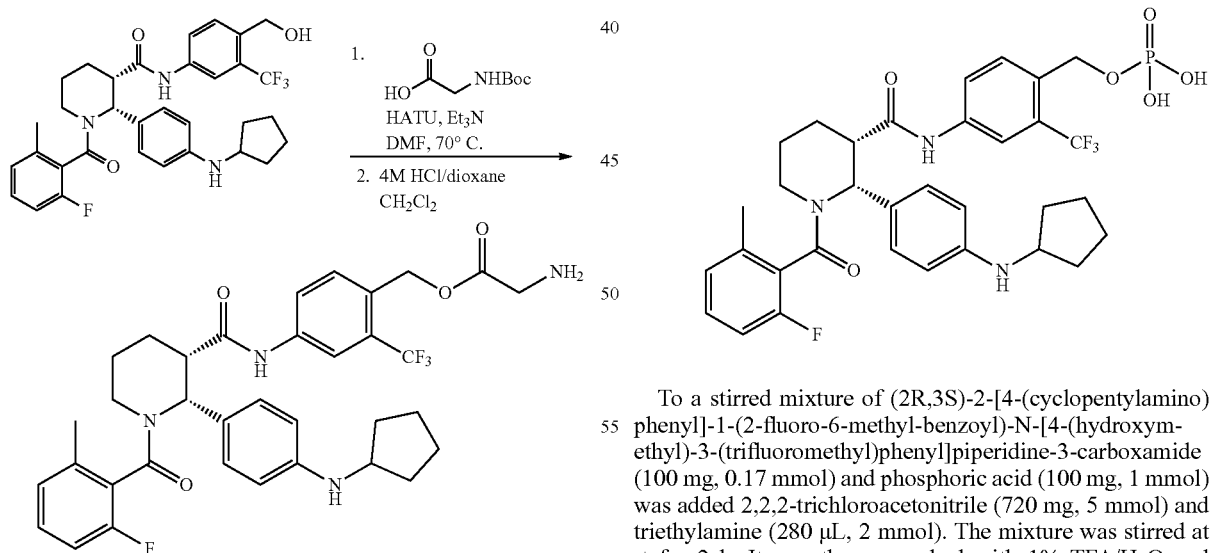

To a stirred solution of (2R,3S)-2-[4-(cyclopentylamino)phenyl]-1-(2-fluoro-6-methyl-benzoyl)-N-[4-(hydroxymethyl)-3-(trifluoromethyl)phenyl]piperidine-3-carboxamide (100 mg, 0.17 mmol) and 2-(tert-butoxycarbonylamino)acetic acid (88 mg, 0.50 mmol) in DMF (2.5 mL) was added HATU (190 mg, 0.50 mmol) and triethylamine (129 μL, 0.92 mmol). The mixture was warmed to 60° C. and stirred for 1 h. It was then cooled to rt, diluted with EtOAc, washed with saturated aqueous NaHCO$_3$ solution and water, and concentrated in vacuo. The crude was purified by silica gel chromatography (0-90% EtOAc/hexane) to obtain 110 mg desired intermediate. This intermediate was dissolved in CH$_2$Cl$_2$ (2 mL) and treated with 4M HCl in dioxane (2 mL) at rt for 45 min. It was then cooled to rt, diluted with EtOAc, washed with saturated NaHCO$_3$ solution and water, and extracted with EtOAc. The crude product was purified by silica gel chromatography (0-20% MeOH/EtOAc) to obtain [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 2-aminoacetate, MS: (ES) m/z calculated for $C_{35}H_{38}F_4N_4O_4$[M+H]$^{+6}$55.3, found 655.3.

Example 21: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl dihydrogen phosphate

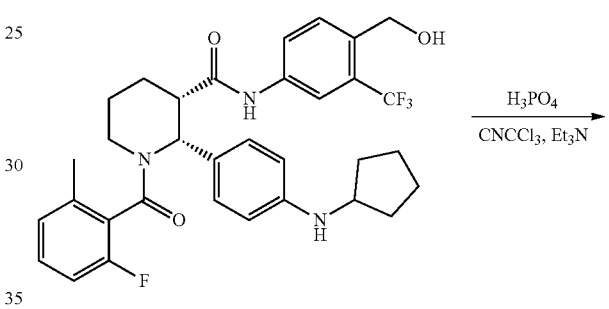

To a stirred mixture of (2R,3S)-2-[4-(cyclopentylamino)phenyl]-1-(2-fluoro-6-methyl-benzoyl)-N-[4-(hydroxymethyl)-3-(trifluoromethyl)phenyl]piperidine-3-carboxamide (100 mg, 0.17 mmol) and phosphoric acid (100 mg, 1 mmol) was added 2,2,2-trichloroacetonitrile (720 mg, 5 mmol) and triethylamine (280 μL, 2 mmol). The mixture was stirred at rt for 2 h. It was then quenched with 1% TFA/H$_2$O and extracted with $^i$PrOH/CHCl$_3$ (1:3). The crude product was purified by silica gel chromatography with a gradient of 0-60% (10% HOAc/MeOH)/CH$_2$Cl$_2$ to yield [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl dihydrogen phosphate, MS: (ES) m/z calculated for $C_{33}H_{36}F_4N_3O_6P$[M+H]$^+$678.3, found 678.3.

Example 22: Synthesis of Disodium salt of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methoxymethyl dihydrogen phosphate

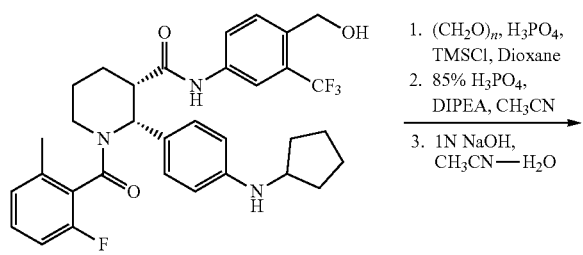

1. (CH₂O)ₙ, H₃PO₄, TMSCl, Dioxane
2. 85% H₃PO₄, DIPEA, CH₃CN
3. 1N NaOH, CH₃CN—H₂O

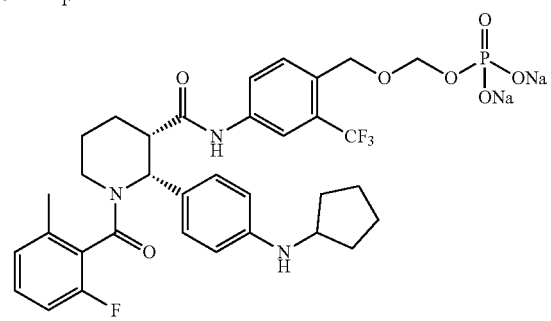

To a stirred suspension of (2R,3S)-2-[4-(cyclopentylamino)phenyl]-1-(2-fluoro-6-methyl-benzoyl)-N-[4-(hydroxymethyl)-3-(trifluoromethyl)phenyl]piperidine-3-carboxamide (598 mg, 1.0 mmol) and paraformaldehyde (120 mg, 4.0 mmol) in dioxane (8 mL) was added chlorotrimethylsilane (8 mL) and phosphoric acid (1.0 g, 10.0 mmol). The reaction was stirred for 9 h and then concentrated in vacuo. The residue was dissolved in CH₃CN (5 mL) and added to a solution of 85% H₃PO₄ in water (1.2 mL), DIPEA (5.2 mL) in CH₃CN (15 mL) at rt. After stirring at rt for 30 min, reaction mixture was concentrated in vacuo. To this crude residue was added water (30 mL) and stirred for 30 min at rt. The obtained solid was filtered, washed with water (10 mL) and dried under high vacuum. The solid was then washed with 1:1 EtOAc-Et₂O (20 mL) to get rid of non-polar impurities. Obtained crude product was purified by preparative HPLC (acetonitrile-water with 0.1% Et₃N) to obtain product as ditrimethylamine salt, which was treated with 0.1M NaOH (11.7 mL) and CH₃CN (12 mL) and lyophilized to obtain disodium salt of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methoxymethyl dihydrogen phosphate, MS: (ES) m/z calculated for $C_{34}H_{38}F_4N_3O_7P[M+H]^+$ 708.2, found 708.2.

Example 23: Synthesis of [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 3-[(4-methylpiperazin-1-yl)methyl]benzoate

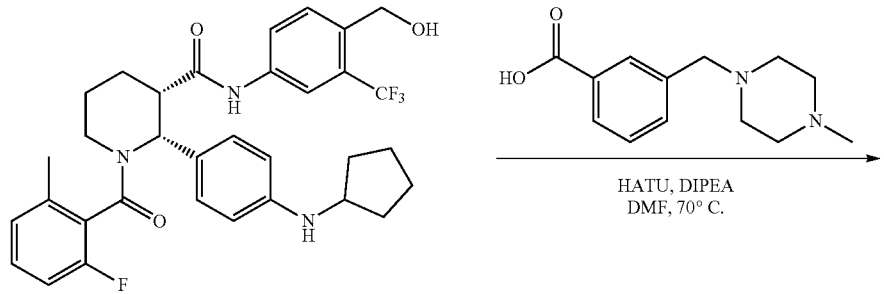

HATU, DIPEA
DMF, 70° C.

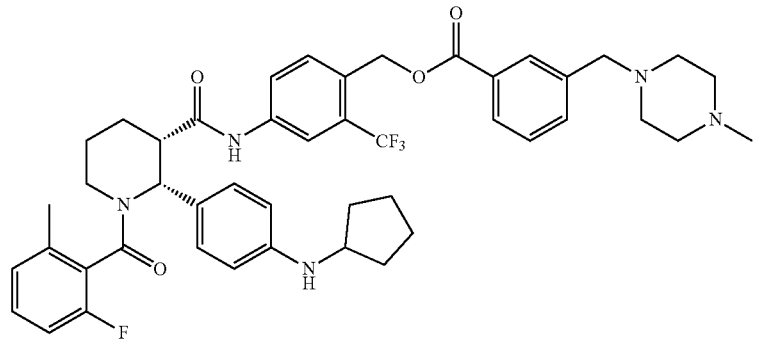

To a stirred solution of (2R,3S)-2-[4-(cyclopentylamino)phenyl]-1-(2-fluoro-6-methyl-benzoyl)-N-[4-(hydroxymethyl)-3-(trifluoromethyl)phenyl]piperidine-3-carboxamide (511 mg, 0.85 mmol) and 3-[(4-methylpiperazin-1-yl)methyl]benzoic acid (200 mg, 0.85 mmol) in DMF (5 mL) was added HATU (485 mg, 1.27 mmol) and N,N-diisopropylethylamine (443 uL, 2.55 mmol). The mixture was warmed up to 70° C. and stirred for 2 h. Then it was cooled down to rt, diluted with EtOAc, washed with saturated NaHCO$_3$ solution and water, and concentrated in vacuo. The crude was purified by silica gel chromatography (0-20% MeOH/CH$_2$Cl$_2$) to obtain [4-[[(2R,3S)-2-[4-(cyclopentylamino)phenyl]-1-(2-fluoro-6-methyl-benzoyl)piperidine-3-carbonyl]amino]-2-(trifluoromethyl)phenyl]methyl 3-[(4-methylpiperazin-1-yl)methyl]benzoate. MS: (ES) m/z calculated for $C_{46}H_{51}F_4N_5O_4[M+H]^+$ 814.3, found 814.8.

Example 24: Solubility of Compounds

The solubility of the compounds below was obtained by dispensing indicated arbitrary amount of the compound in 1 mL of Milli-Q water at room temperature and by examining it with naked eye after shaking the vial thoroughly. Experiments with no visible particles by naked eye were considered as clear solutions. It is important to note that the reported solubility information is not the maximum solubility of the compounds in water.

| Example Compound No. | Structure | Solubility in H$_2$O |
|---|---|---|
| 1 | 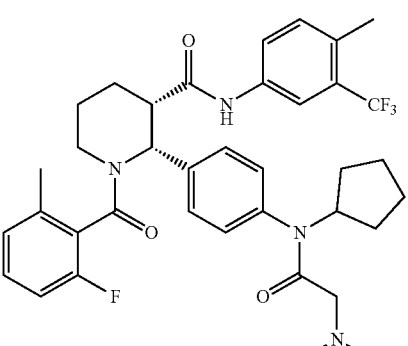 (HCl salt) | >10 mg/mL |
| 2 | 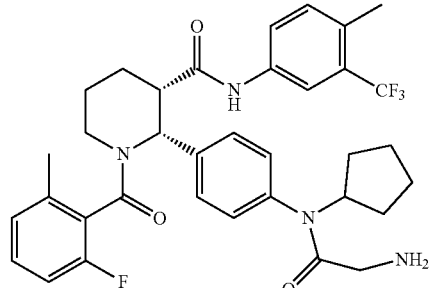 (HCl salt) | >5 mg/mL |
| 9 | 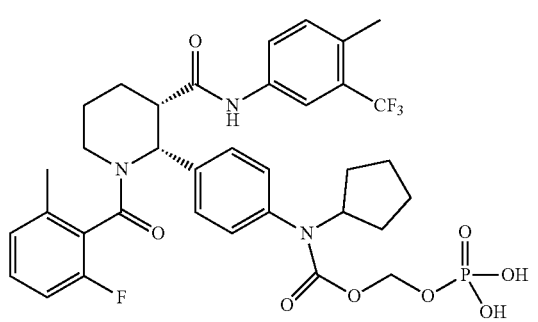 (di Na salt) | >10 mg/mL |

-continued
| Example Compound No. | Structure | Solubility in H₂O |
|---|---|---|
| 3 | 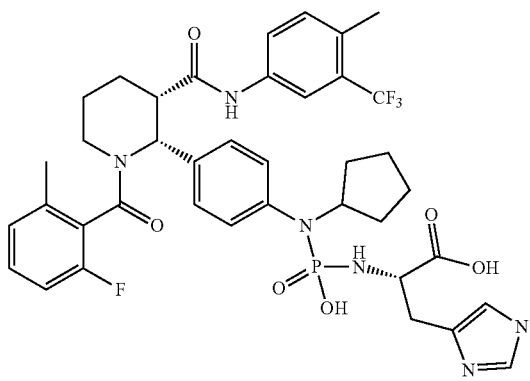<br>(HCl salt) | 5 mg/mL |
| 4 | 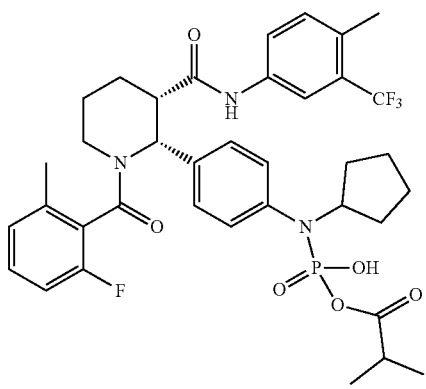<br>(Na salt) | 1 mg/mL |
| 10 | 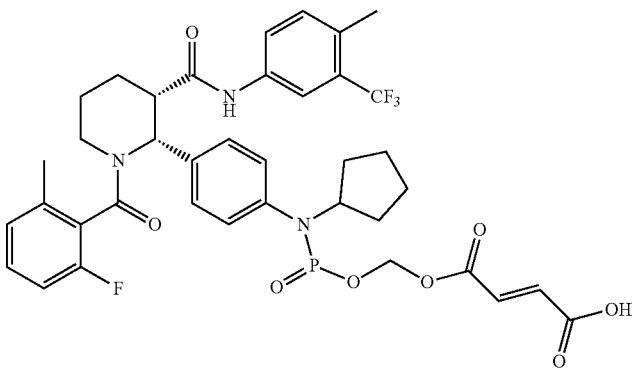<br>(Na salt) | 1 mg/mL |

-continued
| Example Compound No. | Structure | Solubility in H₂O |
|---|---|---|
| 5 | 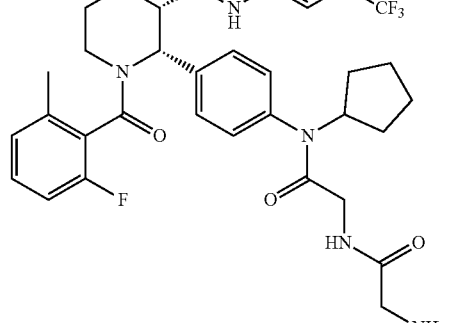<br>(HCl salt) | 10 mg/mL |
| 11 | 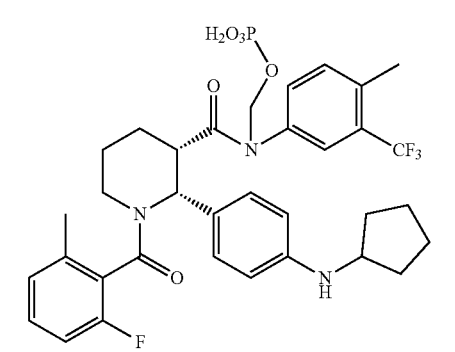<br>(di Na salt) | >5 mg/mL |
| 6 | 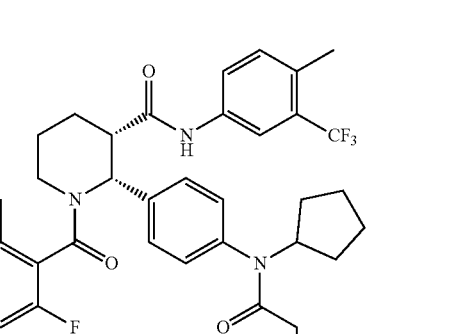<br>(HCl salt) | 5 mg/mL |

-continued

| Example Compound No. | Structure | Solubility in H₂O |
|---|---|---|
| 7 | (HCl salt) | 1-2 mg/mL |
| 8 | (di Na salt) | 1 mg/mL |

| Compound Id | Structure | Solubility in H₂O |
|---|---|---|
| 20 | (HCl salt) | >10 mg/mL |

-continued
| Compound Id | Structure | Solubility in H₂O |
|---|---|---|
| 22 | 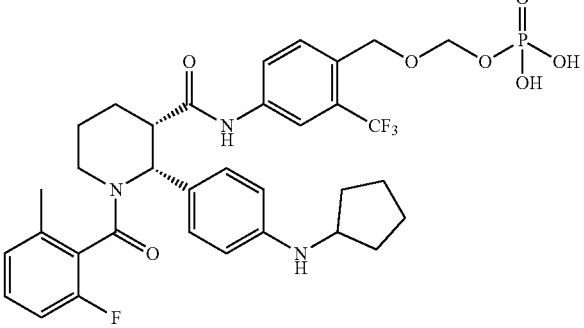<br>(di Na salt) | 15 mg/mL |
| 13 | 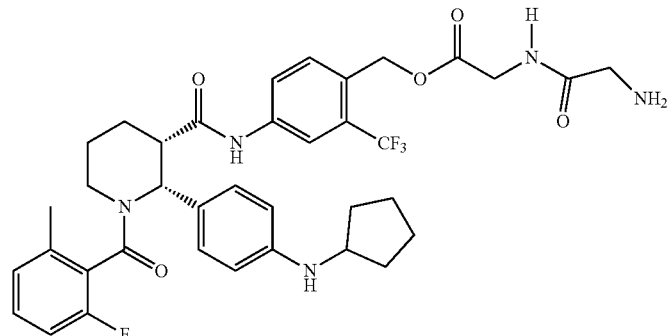<br>(HCl salt) | 10 mg/mL |
| 14 | 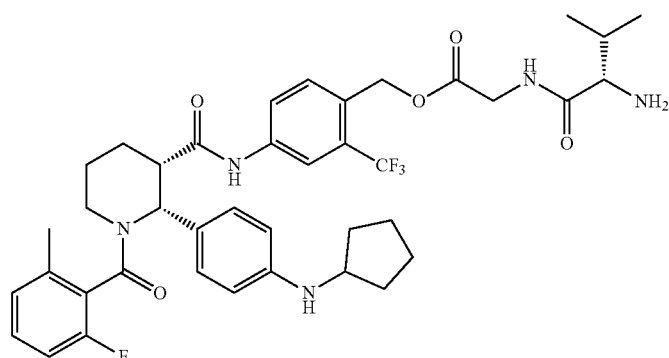<br>(HCl salt) | 5 mg/mL |
| 15 | 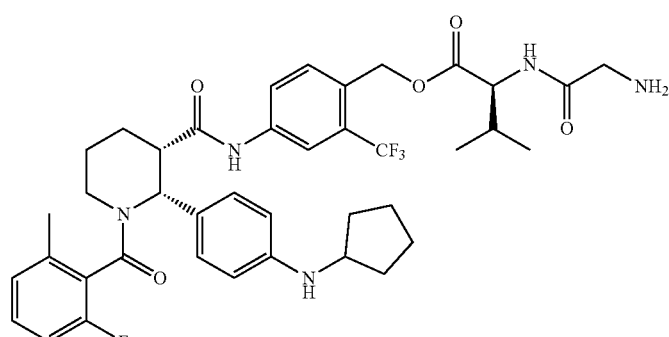<br>(HCl salt) | 5 mg/mL |

-continued
| Compound Id | Structure | Solubility in H$_2$O |
|---|---|---|
| 16 | 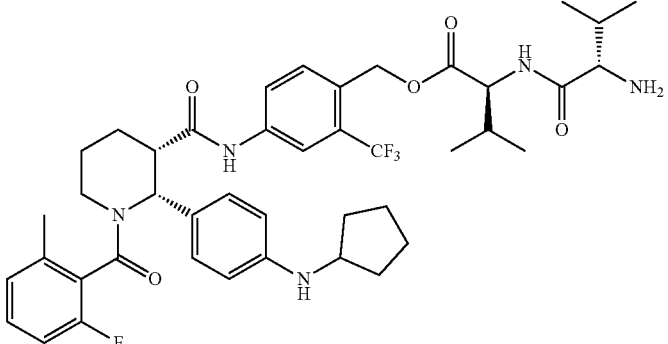<br>(HCl salt) | 5 mg/mL |
| 17 | 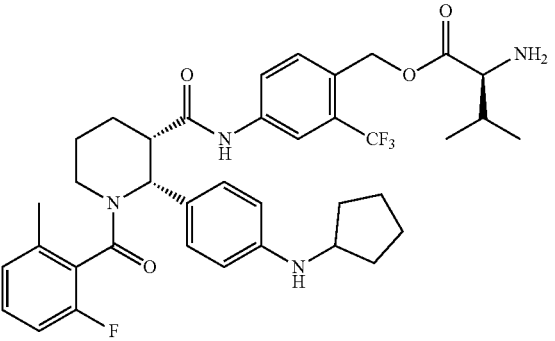<br>(HCl salt) | 4 mg/mL |
| 23 | 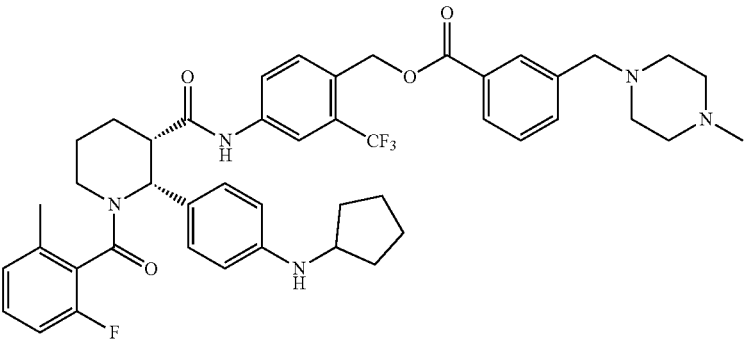<br>(di HCl salt) | >1 mg/mL |
| 18 | 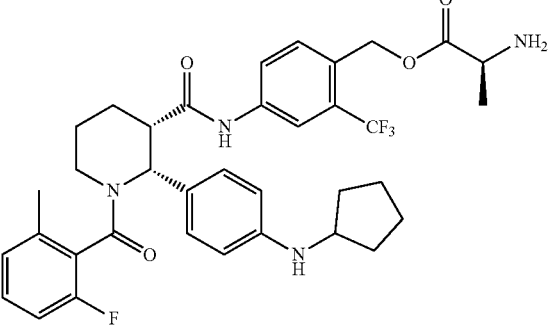<br>(HCl salt) | >5 mg/mL |

The solubility of the first compound in the table below was determined using the following protocol. Saturated solutions of compound in pH 7 buffers were left overnight at room temperature (25° C.) before they were centrifuged. The supernatants were taken out and quantified. Solubility: 0.053 µg/mL.

The solubility of the second compound in the table below was determined using the following protocol. Saturated solutions of compound were freshly prepared by adding 1 mL D.I. water into 0.8 mg compound powder. After shaking at room temperature for 3 hours, the samples were centrifuged under 14000 rpm for 15 minutes twice. The supernatants were carefully taken out and quantified by LC-MS. Solubility: 1.2±0.2 µg/mL (average of four replicates).

| Structure | *average solubility in water (µg/mL) |
|---|---|
| 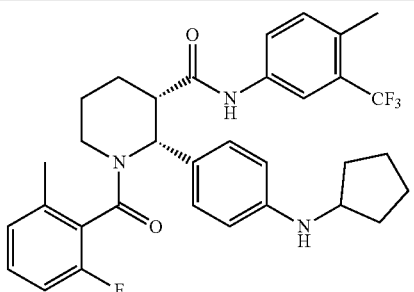 Active compound 1.172 (from WO 2010/07257) | 0.053 |
| 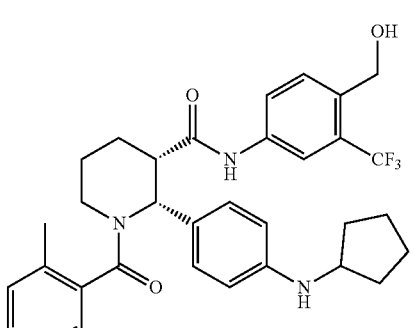 Active compound 1.543 (from WO 2011/163640) | 1.2 |

Example 25: Intravenous Injections in Rats

Male rats, weighing between 0.22 to 0.25 kg, were purchased from Charles River Laboratories (Hollister, Calif.) and were acclimated before use. All compounds were prepared in solution formulations and administered to animals through intravenous dosing. Compound of example 11 was prepared in sterile water and each animal received 1 mL/kg. Compound of example 22 was prepared in 0.9% normal saline and each animal received 1 mL/kg. Blood (0.2 mL) was sampled through the jugular vein or cardiac puncture (for terminal point only) at pre-dose, 2, 5, 10, 15, and 30 min, 1, 2, 4, 6, and 8 hours post-dose for i.v. dosing. Blood samples were collected into chilled polypropylene tubes containing sodium EDTA as the anticoagulant and plasma was collected through centrifugation (Eppendorf Centrifuge 5417R) at 10,000 rpm and 4° C. for 6 minutes and stored at −20° C. until analysis.

Figure 2:
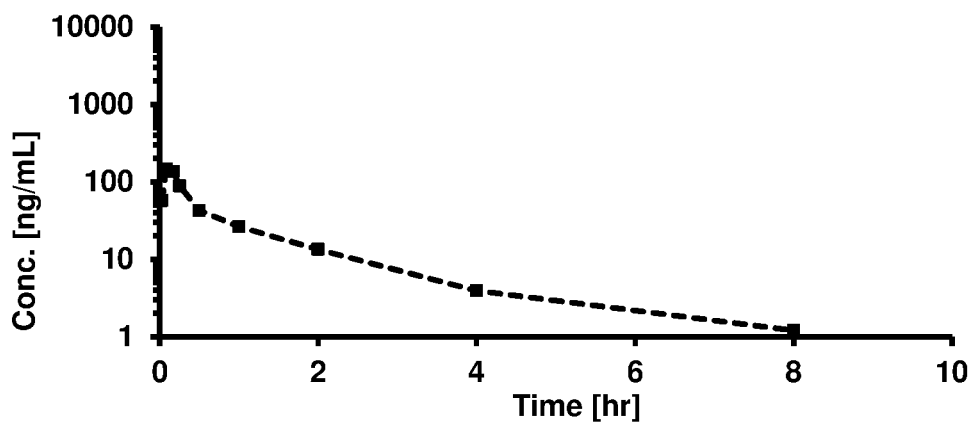
FIG. 2 is a graph showing the release of an active compound 1.172 (from WO 2010/075257) from the compound of Example 11.

Plasma samples (50 µL) were extracted with 150 µL acetonitrile containing an internal standard on a linear shaker for 10 min and then centrifuged at 3700 g for 10 min at 4° C. (Allegra X-15R centrifuge, Beckman Coulter, Inc., Fullerton, Calif.). One hundred µL of the resulting supernatant was transferred into a new plate and mixed with 100 µL 0.1% formic acid in water for LC-MS/MS analysis. Good amounts of active drugs were released after intravenous injection for both compounds in male rats as illustrated by FIGS. 1 and 2.

What is claimed is:

1. A compound of Formula (I)

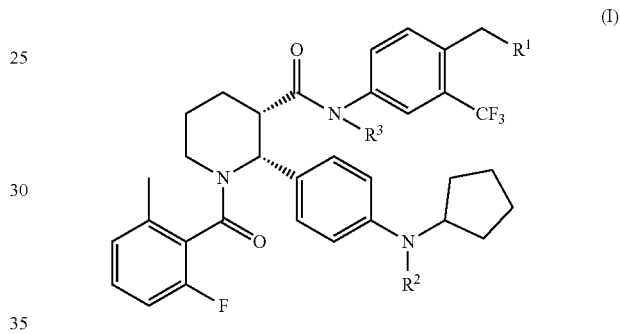

or a pharmaceutically acceptable salt thereof, wherein:

$R^1$ is selected from the group consisting of —O—CH$_2$—O—P(O)OR$^a$OR$^b$, —O—C(O)—C$_{1-6}$ alkylene-L$^2$-X$^1$, —O—P(O)OR$^a$OR$^b$, and —O—C(O)-A$^1$-(C$_{1-3}$ alkylene)$_n$-C$_{4-7}$ heterocyclyl wherein the C$_{4-7}$ heterocyclyl is optionally substituted with 1 to 6 R$^c$ groups;

$A^1$ is selected from the group consisting of C$_{6-10}$ aryl, C$_{3-10}$ cycloalkyl, C$_{5-10}$ heteroaryl and C$_{5-10}$ heterocyclyl, each of which is optionally substituted with 1 to 5 R$^x$ which can be the same or different;

n=0 or 1;

$L^2$ is independently selected from the group consisting of a bond, —O—C(O)—C$_{1-6}$ alkylene-, and —NR$^d$—C(O)—C$_{1-6}$ alkylene-;

$X^1$ is independently selected from the group consisting of —NR$^e$R$^f$, —P(O)OR$^a$OR$^b$, —O—P(O)OR$^a$OR$^b$, and —CO$_2$H;

$R^2$ is H;

$R^3$ is H;

each $R^x$ is independently selected from the group consisting of halogen, C$_{1-6}$alkyl, C$_{1-6}$haloalkyl, C$_{1-6}$heteroalkyl, CN, NR$^y$R$^z$, SR$^y$ and OR$^y$;

each $R^c$ is independently selected from the group consisting of halogen, C$_{1-6}$alkyl, C$_{1-6}$haloalkyl, C$_{1-6}$heteroalkyl, CN, NR$^y$R$^z$, SR$^y$ and OR$^y$;

each $R^a$, $R^b$, $R^d$, $R^e$, $R^f$, $R^y$ and $R^z$ is independently selected from the group consisting of H and C$_{1-6}$ alkyl.

2. The compound of claim 1 selected from the group consisting of:

75
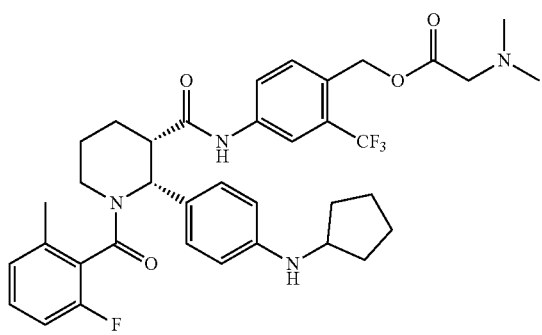 [SMILES: Cc1cccc(F)c1C(=O)N1CCC[C@H](C(=O)Nc2ccc(COC(=O)CN(C)C)c(C(F)(F)F)c2)[C@@H]1c1ccc(NC2CCCC2)cc1]
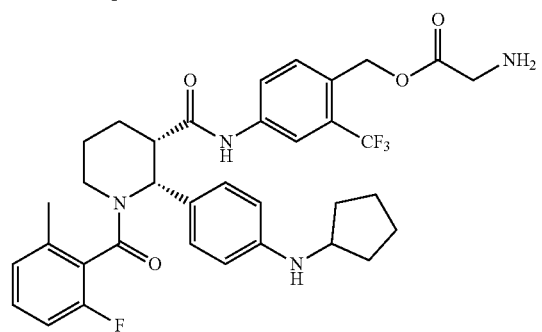
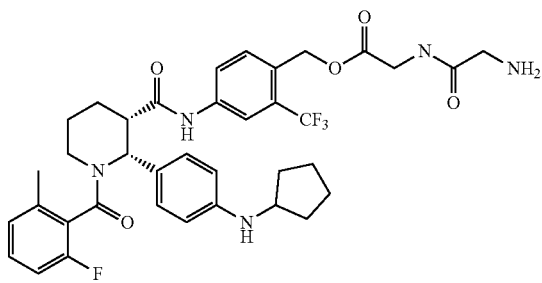 [SMILES: Cc1cccc(F)c1C(=O)N1CCC[C@H](C(=O)Nc2ccc(COC(=O)CNC(=O)CN)c(C(F)(F)F)c2)[C@@H]1c1ccc(NC2CCCC2)cc1]
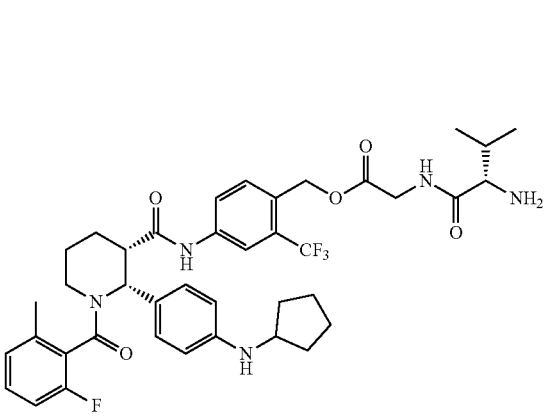 [SMILES: Cc1cccc(F)c1C(=O)N1CCC[C@H](C(=O)Nc2ccc(COC(=O)CNC(=O)[C@@H](N)C(C)C)c(C(F)(F)F)c2)[C@@H]1c1ccc(NC2CCCC2)cc1]
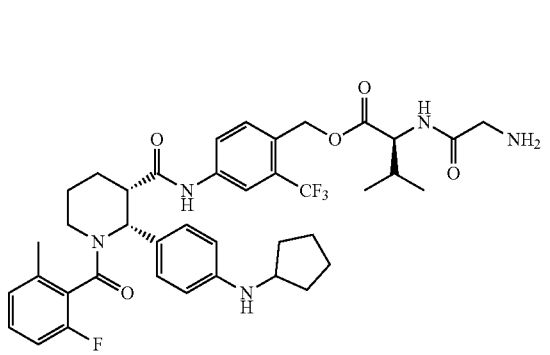 [SMILES: Cc1cccc(F)c1C(=O)N1CCC[C@H](C(=O)Nc2ccc(COC(=O)[C@@H](NC(=O)CN)C(C)C)c(C(F)(F)F)c2)[C@@H]1c1ccc(NC2CCCC2)cc1]
76
-continued
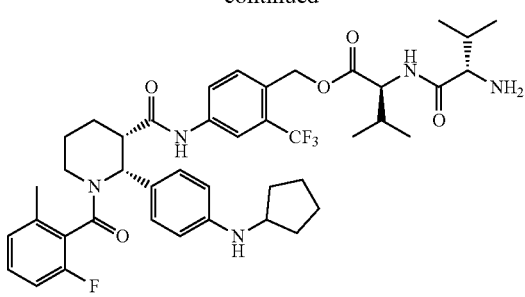
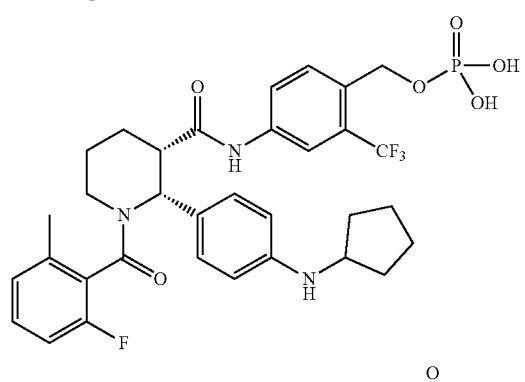
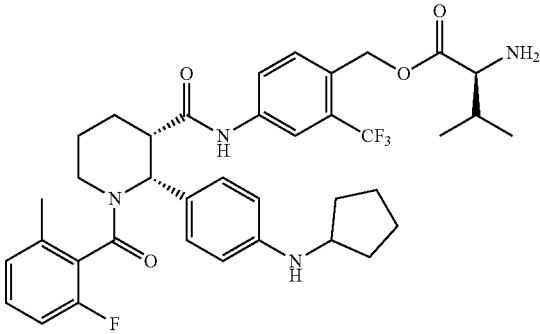
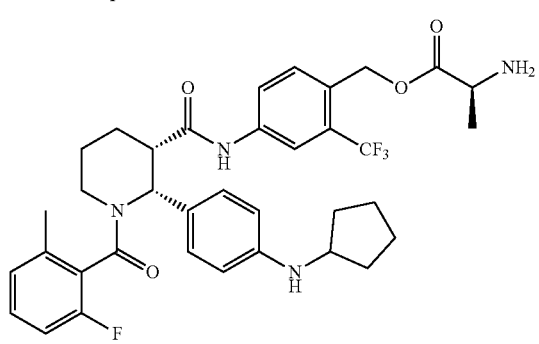
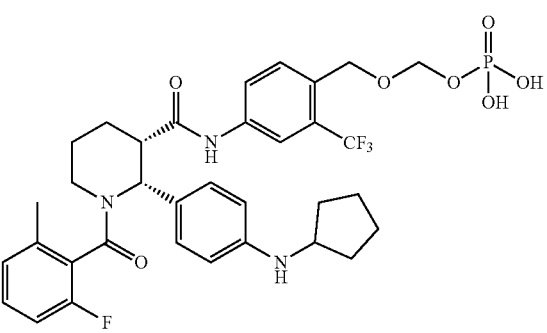

-continued

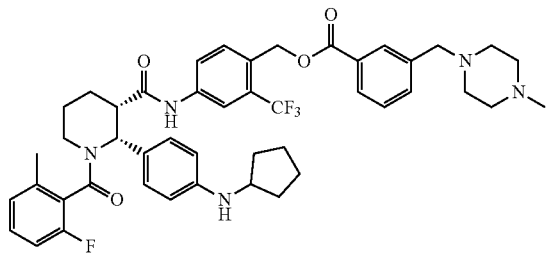

or a pharmaceutically acceptable salt thereof.

3. The compound of claim 1, which is in the form of a pharmaceutically acceptable salt.

4. A pharmaceutical composition comprising a compound of claim 1, or a pharmaceutically acceptable salt thereof, and a pharmaceutically acceptable excipient.

5. The pharmaceutical composition of claim 4, formulated for intravenous, transdermal or subcutaneous administration.

6. A compound of claim 1, having the formula

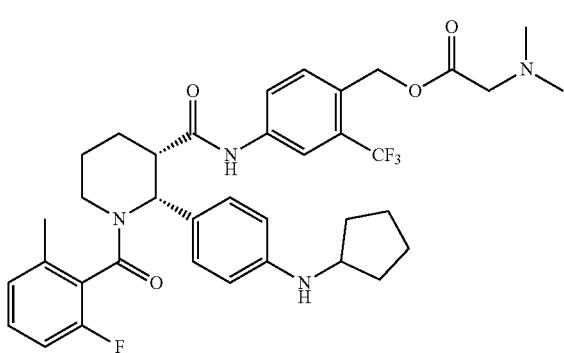

or a pharmaceutically acceptable salt thereof.

7. A compound of claim 1, having the formula

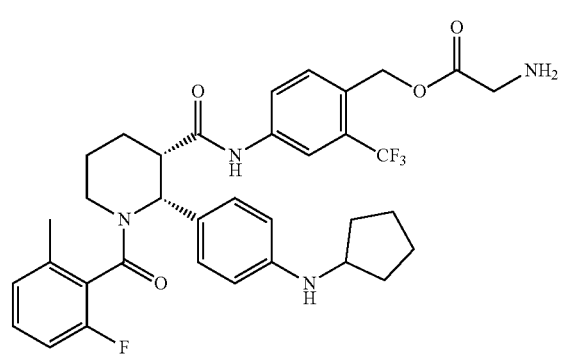

or a pharmaceutically acceptable salt thereof.

8. A compound of claim 1, having the formula

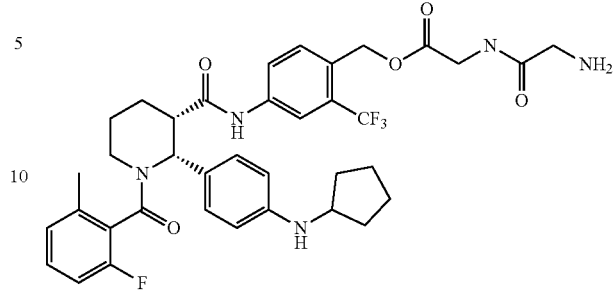

or a pharmaceutically acceptable salt thereof.

9. A compound of claim 1, having the formula

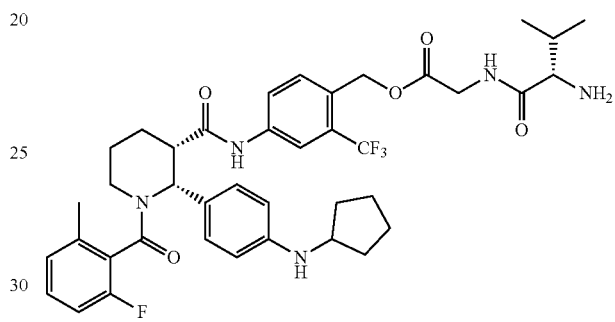

or a pharmaceutically acceptable salt thereof.

10. A compound of claim 1, having the formula

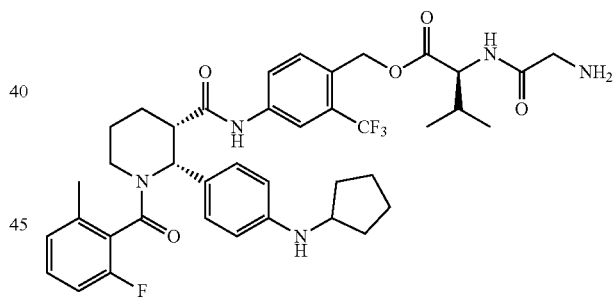

or a pharmaceutically acceptable salt thereof.

11. A compound of claim 1, having the formula

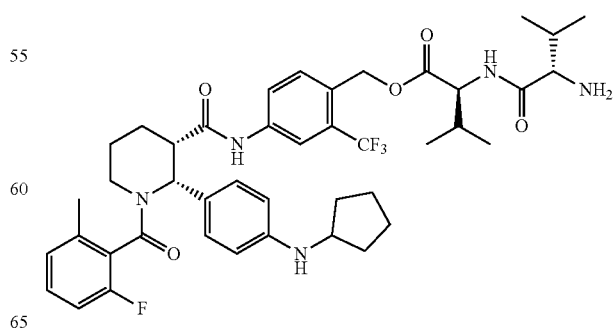

or a pharmaceutically acceptable salt thereof.

12. A compound of claim 1, having the formula

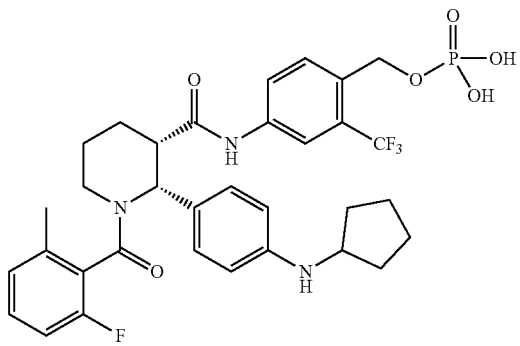 [SMILES: Cc1cccc(F)c1C(=O)N1CCC[C@H](C(=O)Nc2ccc(COP(=O)(O)O)c(C(F)(F)F)c2)[C@@H]1c1ccc(NC2CCCC2)cc1]

or a pharmaceutically acceptable salt thereof.

13. A compound of claim 1, having the formula

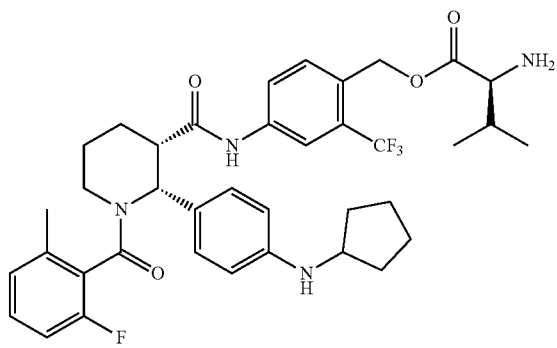 [SMILES: Cc1cccc(F)c1C(=O)N1CCC[C@H](C(=O)Nc2ccc(COC(=O)[C@@H](N)C(C)C)c(C(F)(F)F)c2)[C@@H]1c1ccc(NC2CCCC2)cc1]

or a pharmaceutically acceptable salt thereof.

14. A compound of claim 1, having the formula

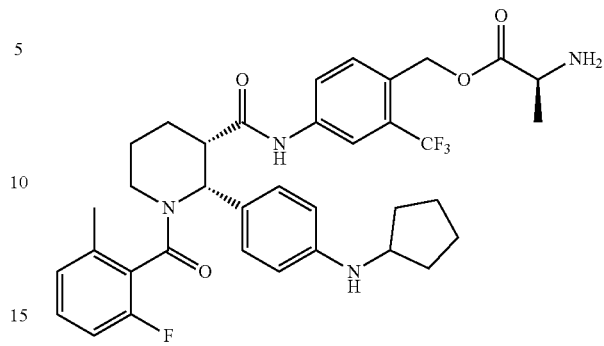

or a pharmaceutically acceptable salt thereof.

15. A compound of claim 1, having the formula

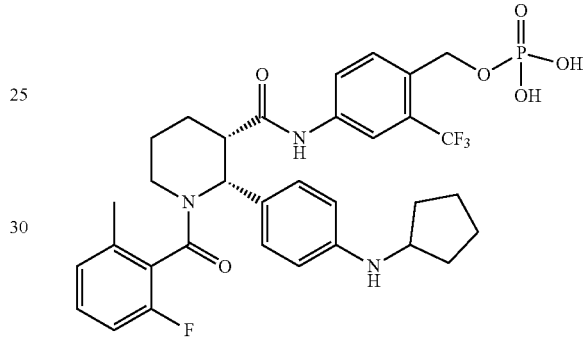

or a pharmaceutically acceptable salt thereof.

16. A compound of claim 1, having the formula

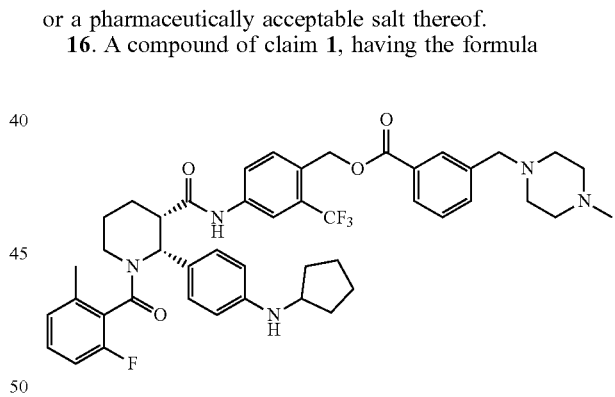

or a pharmaceutically acceptable salt thereof.

* * * * *